United States Patent
Omarsson et al.

(10) Patent No.: US 12,109,139 B2
(45) Date of Patent: Oct. 8, 2024

(54) ORTHOPEDIC DEVICE FOR PATELLOFEMORAL ISSUES

(71) Applicant: Ossur Iceland ehf, Reykjavik (IS)

(72) Inventors: Bjorn Omarsson, Reykjavik (IS); Sindri Pall Sigurdsson, Reykjavik (IS); Guillaume Duport, Reykjavik (IS); Tomas Njalsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 17/969,995

(22) Filed: Oct. 20, 2022

(65) Prior Publication Data

US 2023/0042470 A1 Feb. 9, 2023

Related U.S. Application Data

(63) Continuation of application No. 16/722,737, filed on Dec. 20, 2019, now Pat. No. 11,497,642.

(60) Provisional application No. 62/798,599, filed on Jan. 30, 2019, provisional application No. 62/861,731, filed on Jun. 14, 2019.

(51) Int. Cl.
*A61F 5/01* (2006.01)

(52) U.S. Cl.
CPC .................. *A61F 5/0109* (2013.01)

(58) Field of Classification Search
CPC .... A61F 5/00; A61F 5/05; A61F 5/013; A61F 5/0102; A61F 5/0109; A61F 5/0123; A61F 5/0125; A61F 5/30; A61F 2005/0132; A61F 2005/0137; A61F 2005/0139; A61F 2005/0146; A61F 2005/0155; A61F 2005/0158; A61F 2005/0165; A61F 2005/0167; A61F 2005/0169; A61F 2005/0174; A61F 2005/0175; A61F 2005/0176; A61F 2005/0179; A61F 2005/0181; A61F 2005/0197; A61F 13/062
See application file for complete search history.

(56) References Cited

U.S. PATENT DOCUMENTS

| | | | |
|---|---|---|---|
| 1,622,211 A | 3/1927 | Sheehan |
| 1,666,846 A | 4/1928 | Cooper |
| 3,473,527 A | 10/1969 | Spiro |

(Continued)

FOREIGN PATENT DOCUMENTS

| | | |
|---|---|---|
| DE | 1024204 B | 2/1958 |
| DE | 2724586 A1 | 12/1978 |

(Continued)

OTHER PUBLICATIONS

Product Information, "BORT AsymmetricPlus, No. 114900, Unit PCE", downloaded Mar. 31, 2014, 3 pages. Retrieved at http://shop.bort.de/en/produkt-details.aspx?ProductNo=114900.

(Continued)

*Primary Examiner* — Alireza Nia
*Assistant Examiner* — Gina McCarthy
(74) *Attorney, Agent, or Firm* — Workman Nydegger

(57) ABSTRACT

A patellofemoral support comprises a sleeve and a strap assembly. The strap assembly is arranged to extend helically about the sleeve. A buttress is arranged to removably secure to an inside surface of a first portion of the strap assembly or to the sleeve.

16 Claims, 10 Drawing Sheets

(56) References Cited

U.S. PATENT DOCUMENTS

| | | | |
|---|---|---|---|
| 3,581,741 A | 6/1971 | Rosman et al. | |
| 3,786,804 A | 1/1974 | Lewis | |
| 3,804,084 A | 4/1974 | Lehman | |
| 3,817,244 A | 6/1974 | Taylor | |
| 3,902,482 A | 9/1975 | Taylor | |
| 3,945,046 A | 3/1976 | Stromgren | |
| 4,024,584 A | 5/1977 | Smith | |
| 4,064,874 A | 12/1977 | Valin | |
| 4,084,584 A | 4/1978 | Detty | |
| 4,116,236 A | 9/1978 | Albert | |
| 4,176,665 A | 12/1979 | Terpening | |
| 4,201,203 A * | 5/1980 | Applegate | A61F 5/0109 2/24 |
| 4,287,884 A | 9/1981 | Applegate | |
| 4,287,885 A | 9/1981 | Applegate | |
| 4,296,774 A | 10/1981 | Palumbo | |
| 4,353,362 A | 10/1982 | Demarco | |
| 4,366,813 A * | 1/1983 | Nelson | A61F 5/0109 2/24 |
| 4,370,978 A | 2/1983 | Palumbo | |
| 4,378,009 A | 3/1983 | Rowley et al. | |
| 4,379,463 A | 4/1983 | Meier et al. | |
| 4,423,720 A | 1/1984 | Meier et al. | |
| 4,425,912 A | 1/1984 | Harper | |
| 4,445,505 A | 5/1984 | Labour et al. | |
| 4,466,428 A | 8/1984 | McCoy | |
| 4,490,855 A | 1/1985 | Figgie, III et al. | |
| 4,506,661 A | 3/1985 | Foster | |
| 4,607,628 A | 8/1986 | Dashefsky | |
| 4,651,722 A | 3/1987 | Karczewski | |
| 4,697,583 A | 10/1987 | Mason et al. | |
| 4,700,698 A | 10/1987 | Kleylein | |
| 4,854,308 A | 8/1989 | Drillio | |
| 4,870,956 A | 10/1989 | Fatool et al. | |
| 4,872,448 A | 10/1989 | Johnson, Jr. | |
| 4,887,590 A | 12/1989 | Logue et al. | |
| 4,938,207 A | 7/1990 | Vargo | |
| 4,941,462 A | 7/1990 | Lindberg | |
| 4,986,263 A | 1/1991 | Dickerson et al. | |
| 5,002,045 A | 3/1991 | Spademan | |
| 5,016,621 A | 5/1991 | Bender | |
| 5,024,216 A | 6/1991 | Shiono | |
| 5,036,837 A | 8/1991 | Mitchell et al. | |
| 5,139,447 A | 8/1992 | Peters | |
| 5,167,612 A | 12/1992 | Bonutti | |
| 5,221,252 A | 6/1993 | Caprio, Jr. et al. | |
| 5,230,697 A | 7/1993 | Castillo et al. | |
| 5,261,871 A | 11/1993 | Greenfield | |
| 5,267,951 A | 12/1993 | Ishii | |
| 5,277,697 A | 1/1994 | France et al. | |
| 5,302,169 A | 4/1994 | Taylor | |
| 5,334,135 A | 8/1994 | Grim et al. | |
| 5,383,843 A | 1/1995 | Watson et al. | |
| 5,385,538 A | 1/1995 | Mann | |
| 5,399,153 A * | 3/1995 | Caprio, Jr. | A61F 5/0106 602/26 |
| 5,411,037 A | 5/1995 | Hess et al. | |
| 5,417,646 A | 5/1995 | Gauvry | |
| 5,419,161 A | 5/1995 | Bodenschatz et al. | |
| 5,451,201 A | 9/1995 | Prengler | |
| 5,462,517 A | 10/1995 | Mann | |
| 5,472,413 A | 12/1995 | Detty | |
| 5,512,039 A | 4/1996 | White | |
| 5,527,267 A | 6/1996 | Billotti | |
| 5,538,488 A | 7/1996 | Villepigue | |
| 5,554,105 A | 9/1996 | Taylor | |
| 5,599,288 A | 2/1997 | Shirley et al. | |
| 5,613,943 A * | 3/1997 | Palumbo | A61F 13/062 602/26 |
| 5,626,557 A | 5/1997 | Mann | |
| 5,695,452 A | 12/1997 | Grim et al. | |
| 5,711,312 A | 1/1998 | Staudinger | |
| 5,728,057 A | 3/1998 | Ouellette et al. | |
| 5,730,710 A | 3/1998 | Eichhorn et al. | |
| 5,759,167 A | 6/1998 | Shields, Jr. et al. | |
| 5,769,809 A | 6/1998 | Witzel | |
| 5,792,084 A | 8/1998 | Wilson et al. | |
| 5,797,864 A | 8/1998 | Taylor | |
| 5,807,298 A | 9/1998 | Palumbo | |
| 5,865,776 A * | 2/1999 | Springs | A61F 5/0109 602/26 |
| 5,873,848 A | 2/1999 | Fulkerson | |
| 6,149,616 A | 11/2000 | Szlema et al. | |
| 6,238,360 B1 | 5/2001 | Gildersleeve et al. | |
| D444,563 S * | 7/2001 | Rodgers | D24/190 |
| 6,287,269 B1 | 9/2001 | Osti et al. | |
| 6,336,909 B1 | 1/2002 | Gildersleeve et al. | |
| 6,436,066 B1 | 8/2002 | Lockhart | |
| 6,551,264 B1 | 4/2003 | Cawley et al. | |
| 6,592,539 B1 | 7/2003 | Einarsson et al. | |
| 6,634,190 B2 | 10/2003 | Didier-Laurent | |
| 7,004,919 B2 | 2/2006 | Gaylord et al. | |
| 7,011,641 B1 | 3/2006 | Detoro et al. | |
| 7,060,045 B2 | 6/2006 | Mason et al. | |
| 7,083,586 B2 | 8/2006 | Simmons et al. | |
| 7,198,610 B2 | 4/2007 | Ingimundarson et al. | |
| 7,273,464 B2 | 9/2007 | Reinhardt | |
| D574,084 S | 7/2008 | Reinhardt | |
| 7,473,236 B1 | 1/2009 | Mathewson | |
| 7,517,331 B2 | 4/2009 | Reinhardt et al. | |
| 7,597,675 B2 | 10/2009 | Ingimundarson et al. | |
| 7,625,350 B2 | 12/2009 | Hunter et al. | |
| 7,662,122 B2 | 2/2010 | Sterling | |
| 7,713,225 B2 | 5/2010 | Ingimundarson et al. | |
| 7,749,181 B2 | 7/2010 | Simmons et al. | |
| 7,794,418 B2 | 9/2010 | Ingimundarson et al. | |
| 7,806,842 B2 | 10/2010 | Stevenson et al. | |
| 7,819,830 B2 | 10/2010 | Sindel et al. | |
| 7,862,528 B2 | 1/2011 | Scott | |
| 7,867,183 B2 | 1/2011 | Kazmierczak et al. | |
| 7,896,827 B2 | 3/2011 | Ingimundarson et al. | |
| 7,959,590 B2 | 6/2011 | Scott | |
| 8,025,632 B2 | 9/2011 | Einarsson | |
| 8,043,242 B2 | 10/2011 | McSpadden et al. | |
| 8,048,014 B2 | 11/2011 | Brown | |
| 8,066,654 B2 | 11/2011 | Sandifer et al. | |
| 8,118,765 B2 | 2/2012 | Magnusson | |
| 8,328,747 B2 | 12/2012 | Matsunaga | |
| 8,784,349 B1 | 7/2014 | Nelson | |
| 9,532,895 B2 | 1/2017 | Romo | |
| 9,744,063 B2 | 8/2017 | Huffa et al. | |
| 2002/0133108 A1 | 9/2002 | Jagodzinski | |
| 2003/0204156 A1 | 10/2003 | Nelson et al. | |
| 2004/0054307 A1 | 3/2004 | Mason et al. | |
| 2004/0153017 A1* | 8/2004 | Simmons | A61F 5/0109 602/26 |
| 2004/0176715 A1 | 9/2004 | Nelson | |
| 2004/0225245 A1* | 11/2004 | Nelson | A61F 5/0123 602/26 |
| 2005/0004499 A1 | 1/2005 | Bauerfeind et al. | |
| 2005/0020951 A1 | 1/2005 | Gaylord et al. | |
| 2005/0038367 A1 | 2/2005 | McCormick et al. | |
| 2007/0060853 A1 | 3/2007 | Sindel et al. | |
| 2008/0139985 A1 | 6/2008 | Gilmour | |
| 2009/0076426 A1 | 3/2009 | Einarsson et al. | |
| 2009/0131844 A1 | 5/2009 | Dean et al. | |
| 2009/0156973 A1 | 6/2009 | Scott | |
| 2010/0036303 A1 | 2/2010 | Bauerfeind et al. | |
| 2011/0098618 A1 | 4/2011 | Fleming | |
| 2011/0137220 A1 | 6/2011 | Vollbrecht et al. | |
| 2012/0165714 A1* | 6/2012 | Forbes | A61F 5/0109 602/26 |
| 2012/0277649 A1 | 11/2012 | Matsuo et al. | |
| 2013/0172797 A1 | 7/2013 | Merkley et al. | |
| 2015/0305908 A1 | 10/2015 | Spade | |
| 2017/0128248 A1 | 5/2017 | Hur | |

FOREIGN PATENT DOCUMENTS

| | | |
|---|---|---|
| DE | 3511250 A1 | 11/1985 |
| DE | 4013693 A1 | 8/1991 |
| EP | 0290409 A1 | 11/1988 |
| EP | 0941722 A1 | 9/1999 |

(56) References Cited

FOREIGN PATENT DOCUMENTS

| | | |
|---|---|---|
| EP | 0809478 B1 | 5/2002 |
| EP | 2283795 A1 | 2/2011 |
| FR | 2486388 A1 | 1/1982 |
| FR | 2807644 A1 | 10/2001 |
| GB | 2136294 A | 9/1984 |
| JP | 2001070329 A | 3/2001 |
| JP | 2009233149 A | 10/2009 |
| WO | 0051537 A1 | 9/2000 |
| WO | 2012003992 A1 | 1/2012 |

OTHER PUBLICATIONS

Product Information, "BORT AsymmetricPlus, No. 114700, Unit PCE", downloaded Mar. 31, 2014, 3 pages. Retrieved at http://shop.bort.de/en/produkt-details.aspx?ProductNo=114700.

Brochure, "BORT Asymmetric Plus, Die Mehrwert-Orthese bei Patella-Luxation", downloaded Aug. 2012. 16 pages. Retrieved at http://www.bort.com.

\* cited by examiner

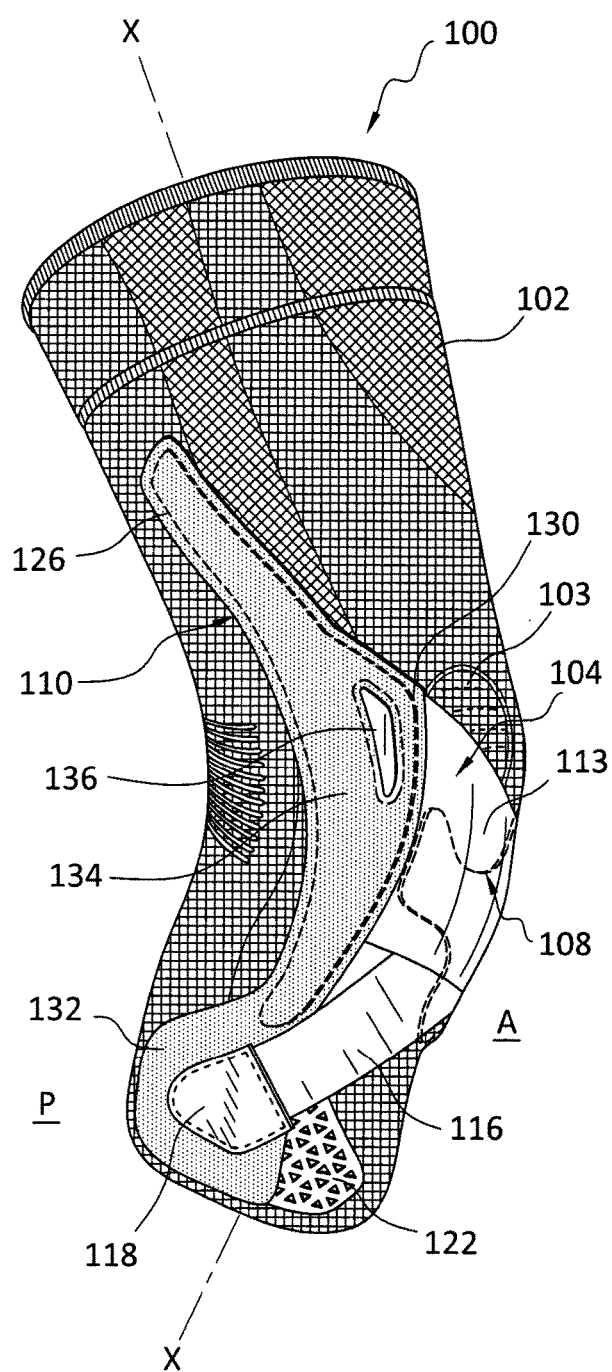
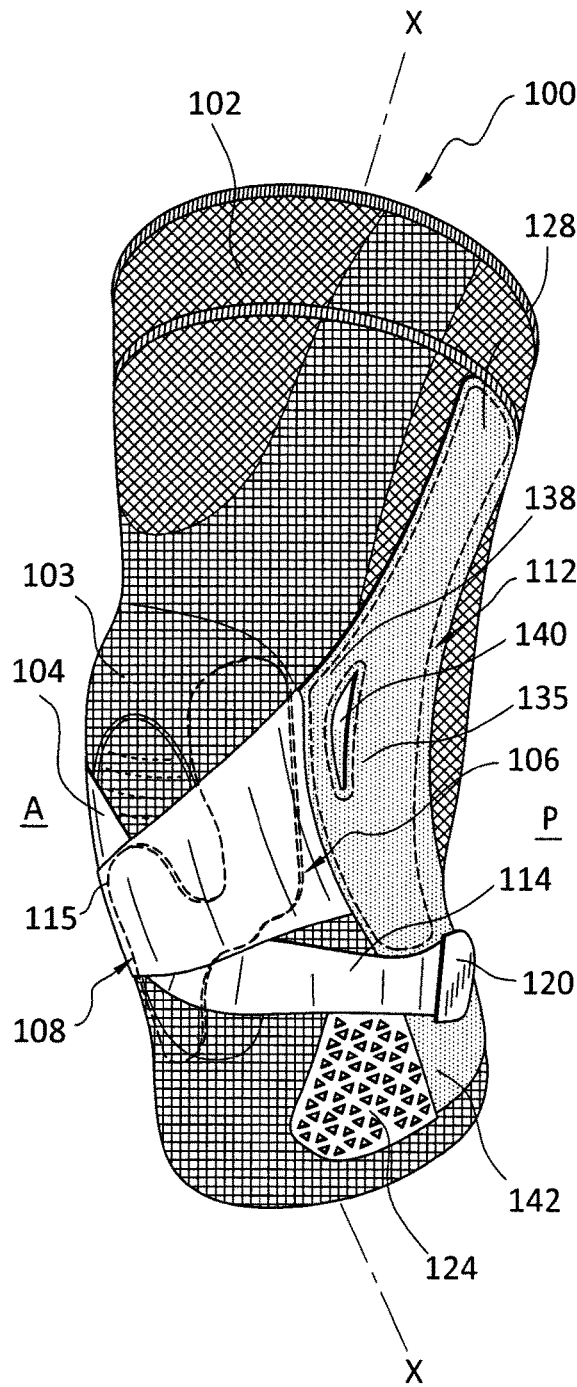
FIG. 1
FIG. 2

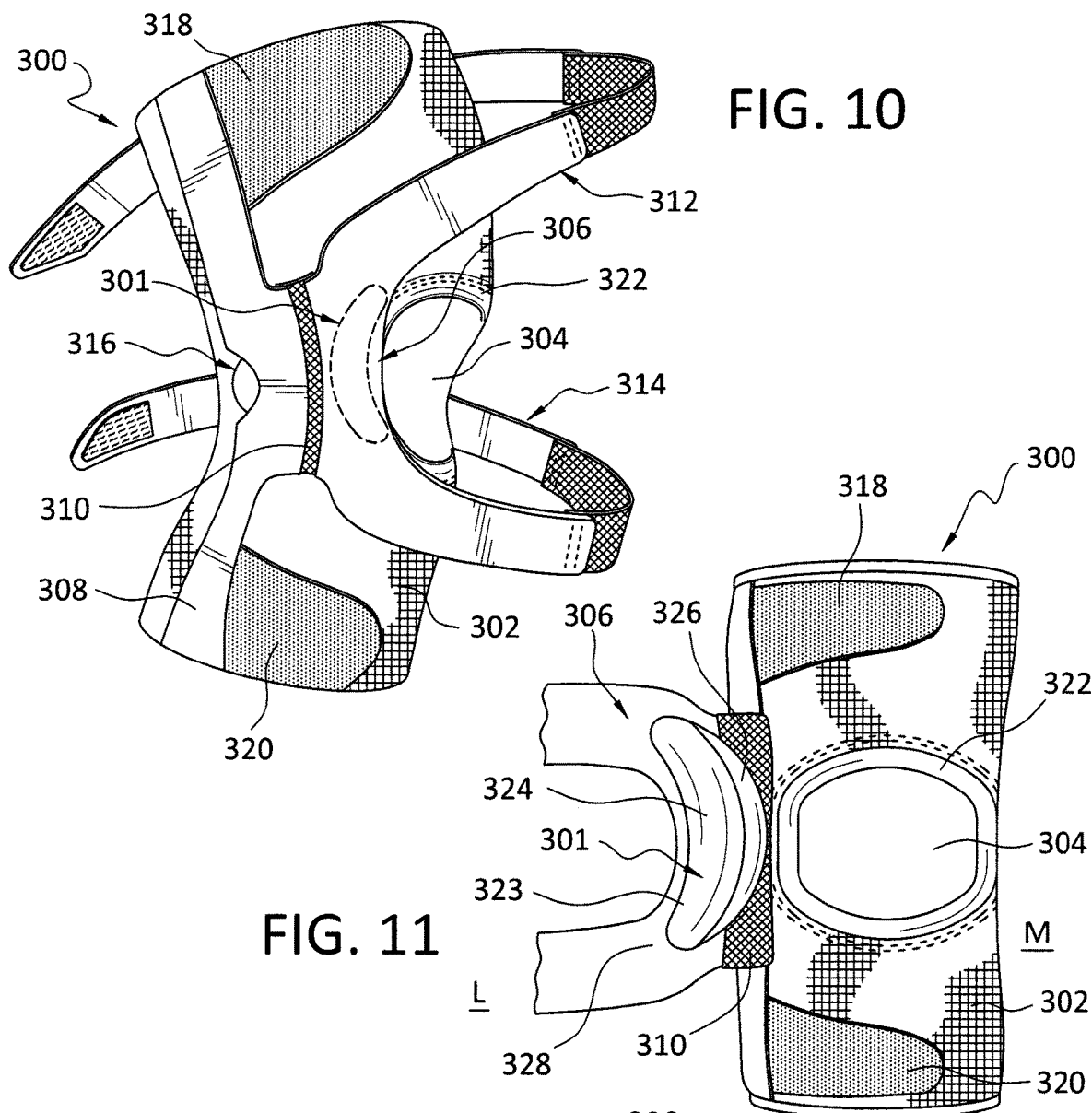

ORTHOPEDIC DEVICE FOR PATELLOFEMORAL ISSUES

FIELD OF THE DISCLOSURE

The disclosure relates to orthopedic devices, and more particularly to an orthopedic device for supporting a patella and treating patellofemoral issues or complications.

BACKGROUND

Orthopedic devices, such as braces, may be used for supporting, protecting, or rehabilitating a portion of a human body, including a limb. Braces may apply straps, buttresses, compression, rigid frames, and other features to enable the user or enhance the user's ability to engage in normal activities while mitigating particular issues or conditions. The patella, commonly known as the kneecap, is at the knee and maintained in place by muscles, tendons, and ligaments, including the patellar tendon which attaches the apex or bottom-most portion of the patella and to the tibia.

An orthopedic device for treating patellofemoral issues or complications may ensure that a patella of a user is maintained in its proper position throughout a range of normal motions, such as walking, sitting, jumping, or otherwise. This may be important for individuals with issues or pathologies such as patellar instability, patellar tracking disorder, subluxation, or other disorders of the knee, which may involve a patella translating or popping out of its proper position, causing pain and discomfort.

Early and existing devices aimed at addressing these pathologies have insufficiently or sub-optimally provided forces to influence the position of the patella relative to a limb. For instance, existing patellofemoral supports may fail to adequately provide both medial and lateral stabilization while applying an amount of pressure to the patellar tendon. Other devices have inadequate side-specific properties because they do not adequately provide an optimal amount of pressure and support proximate a patella on an affected side of the user. With users suffering from patellar tracking disorder, pressure may be needed both on a side of the leg toward which the patella is prone to track particularly during movement, and on portions of the anatomy affected during movement, such as tendons and ligaments.

In certain devices it is also difficult to provide a proper amount of force, particularly during various movements such as extension and flexion, without causing unwanted tracking. Straps or other pressure-imposing features may disadvantageously press the patella out of a desired configuration or may cause discomfort by applying too much pressure, especially at a certain portion of the limb and especially during a certain level of flexion. Compliant use with such devices may be poor and may result in further pain, discomfort, or other issues.

Existing patellofemoral supports also may disadvantageously be difficult to don, expensive, non-durable, and/or uncomfortable. Straps, hinges, buttresses, and other components may be poorly adapted to the dynamic shape and configuration of other components and increase the cost and complexity of a patellofemoral support or lead to poor compliance. Further, existing patellofemoral supports may be poorly adapted or configured to accommodate the dimensions of individual users. The suboptimal arrangement of existing patellofemoral supports has typically required users to undergo significant disruptions to their lifestyle, with numerous activities curtailed, impeded, or otherwise adversely affected.

There is a need for an orthopedic device for patellofemoral issues, such as a patellofemoral support, that overcomes the disadvantages of existing patellofemoral supports and provides an optimized configuration of components for addressing patellar pathologies while optimizing user compliance, comfort, and cost.

SUMMARY

An orthopedic device is accordingly provided to address the drawbacks of existing orthopedic devices for patellofemoral issues, with the exemplary orthopedic device being a patellofemoral support. The patellofemoral support generally comprises a sleeve arranged for surrounding at least a portion of the user's limb and at least over a knee, at least one buttress, and at least one strap system arranged to press or urge the at least one buttress against the patella. The at least one buttress and strap system may be arranged for providing effective pressure and forces on a patella to stabilize or immobilize the patella, particularly in response to a user's individual needs and movements.

The at least one buttress and strap system may be arranged to apply a comfortable and effective amount of pressure on a particular side of a patella. The at least one buttress may comprise first and second branches that extend asymmetrically or symmetrically about opposed sides of the patella, and is arranged to cooperate with the at least one strap system. The strap system may apply comfortable compression about the at least one buttress such as a generally even amount or an otherwise desirable distribution of pressure over the at least one buttress. The at least one buttress may comprise an extension arranged to extend over the patellar tendon, with the strap system arranged to press the extension against the patellar tendon for pain relief and treatment of patellar tendon-related pathologies.

The strap system, although not limited, preferably extends generally from lateral and/or medial sides of the sleeve and over the anterior side of the sleeve. In an exemplary embodiment, the strap system comprises at least one first strap and at least one second strap extending from opposed medial or lateral sides of the sleeve, respectively, and intersecting at least on a distal side of the patella over the at least one buttress so as to secure to an opposite side of the patellofemoral support from which the at least one first and second straps initially extend.

The strap system may not interfere with the posterior side of the sleeve, and may rather isolate compression over the anterior aspect of a user's leg, particularly over the at least one buttress. The strap system may be arranged with suitable securement means, such as tabs having fasteners that may connect to tab landing areas defined on the sleeve, and distinguished from anti-connection portions. The strap system facilitates intuitive and accurate donning and use of the patellofemoral support.

The patellofemoral support may comprise a strap system having at least one helical or diagonal strap and at least one anterior circumferential strap. The at least one helical and anterior circumferential straps may have first ends originating from a same side (i.e., lateral or medial side generally corresponding to the coronal plane) of the patellofemoral support, and second ends terminating on a same second or opposed side of the patellofemoral support. The second ends of the at least one helical and circumferential straps may be joined at a single tab. This arrangement may allow a user to accurately don and tension the device with a single motion, improving and facilitating compliant use, as opposed to managing multiple discrete straps. The anterior circumferential strap may be arranged to extend around a substantial entirety of the sleeve to provide stability against unwanted twisting or migration of the patellofemoral support on a user's leg, such as during donning/doffing and during activities involving significant bending and twisting, such as exercise or outdoor activities.

The sleeve may comprise an elasticized or compressible (about the leg and/or knee) sleeve and the at least one buttress may be formed from a viscoelastic or other compressible material. The at least one buttress may define a profile corresponding or complementary to a shape of a patella and may be pressed against the patella by a strap system having at least one helical strap.

Another embodiment of a patellofemoral support includes a sleeve, a strap assembly having a first portion secured to the sleeve and a second portion removably securable to the sleeve, and at least one buttress securable onto the first portion of the strap assembly. The sleeve may form an opening arranged to correspond to a patella, and the at least one buttress is arranged to secure about a periphery of the opening preferably on either a medial or lateral side of the opening. For example, the at least one buttress may be crescent- or generally semi-circularly shaped, or configured in shape to correspond to only a segment of the opening. The sleeve may define an edging about the periphery of the opening and the edging may have cushioning properties relative to the sleeve outside of the edging. The edging may be selected to vary in width and thickness according to desirable padding features disposed about the knee. The patellofemoral support may have at least one hinge and/or struts along a side portion generally corresponding to a coronal plane.

The at least one buttress is attachable onto an inner surface of the first portion of the strap assembly to be placed adjacent the sleeve, and therefore over or along a portion of the patella for better stabilization. The strap assembly itself carries the at least one buttress and allows a user to position the buttress in combination with positioning of the strap assembly over the sleeve. Compression of the buttress can be achieved according to the tension of the strap assembly about the sleeve and its attachment to the sleeve.

The strap assembly includes at least one strap arranged to extend circumferentially or semi-circumferentially about the sleeve. The at least one strap may extend helically or circumferentially (i.e., generally about an axis of the sleeve) about the sleeve and has a second end forming at least part of the second portion of the strap assembly that is removably securable to the sleeve. The first portion of the at least one strap assembly is permanently secured to the sleeve, and may be connected to sleeve by an elastic segment to transition compression of the at least one buttress and to adapt the tensioning of the strap assembly according to flexion and extension of the knee.

The strap assembly may form a base portion in the first portion which is located between the elastic segment and the at least one strap. The at least one buttress may be supported at the base portion and the at least one strap may extend directly from the base portion. The at least one strap may include at least one elastic segment and at least one substantially inelastic segment, which permits the at least one strap to adapt in tension according to flexion of the knee. In an exemplary embodiment the at least one strap has at least first and second substantially inelastic segments, the at least one elastic segment being located between the at least two inelastic segments.

These and other features of the disclosure will become better understand regarding the following description, appended claims, and accompanying drawings.

BRIEF DESCRIPTION OF THE DRAWINGS

FIG. 1 is a side elevational view of a first side of a patellofemoral support according to an embodiment of the disclosure.

FIG. 2 is a side elevational view of a second side of the patellofemoral support according to FIG. 1.

FIG. 10 is a perspective view of a patellofemoral support according to another embodiment of the disclosure.

FIG. 11 is a front elevational view of the patellofemoral support of FIG. 10.

FIG. 12 is a detail view of the patellofemoral support of FIG. 10.

Figure 1A:
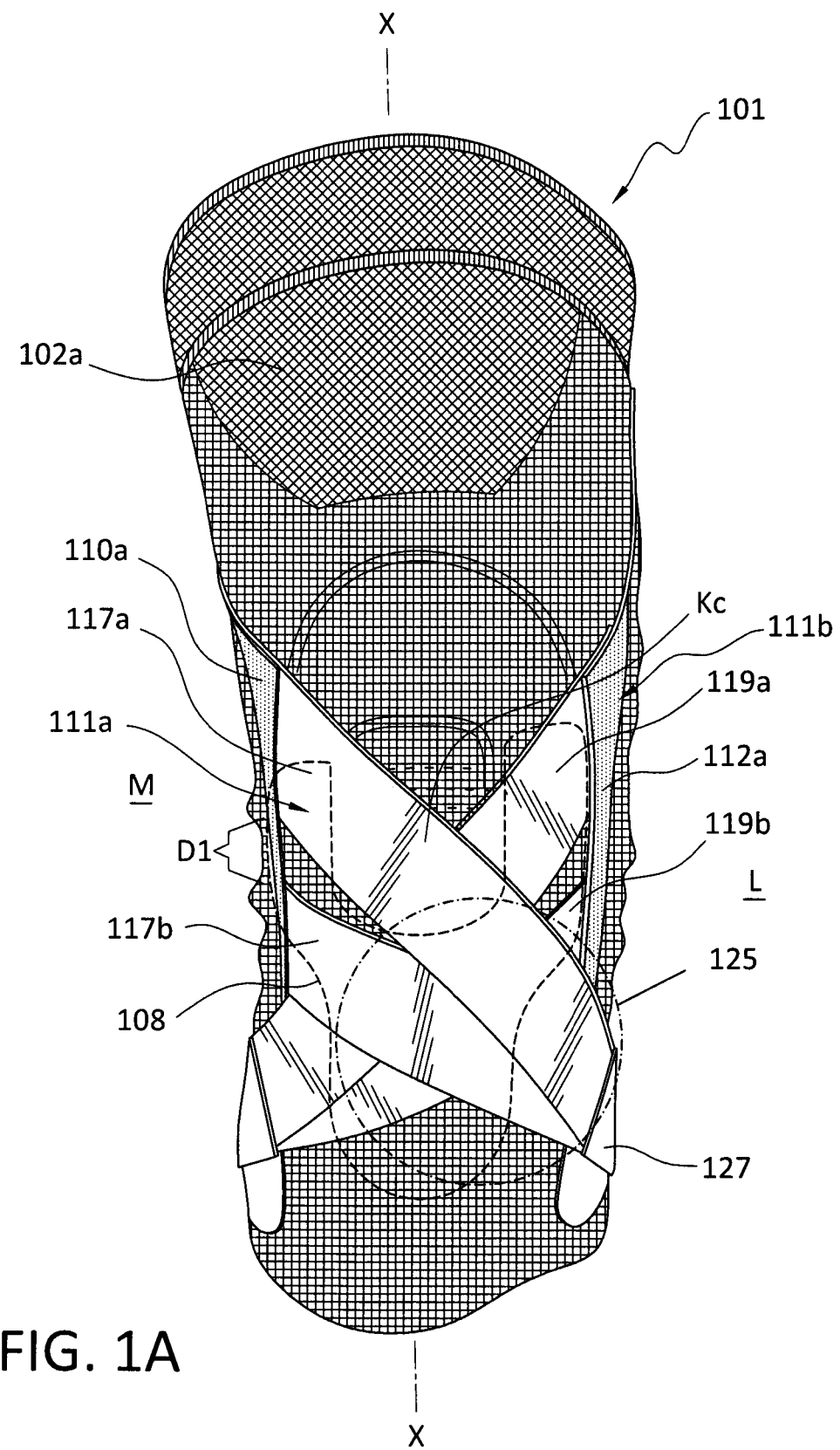
FIG. 1A is a front elevational frontal view of a variation of the patellofemoral support of FIG. 1.

The drawing figures are not necessarily drawn to scale, but instead are drawn to provide a better understanding of the components, and are not intended to be limiting in scope, but to provide exemplary illustrations. The figures illustrate exemplary configurations of an orthopedic device in the form of a patellofemoral support, and in no way limit the structures, configurations, or methods of a patellofemoral support according to the present disclosure.

DETAILED DESCRIPTION OF VARIOUS EMBODIMENTS

An orthopedic device for patellofemoral issues according to embodiments of the disclosure advantageously provides an effective and comfortable device for supporting and/or immobilizing a patella of a user throughout a range of motions and activities with improved attention to the particular needs and pathologies of the user, while enhancing comfort over existing devices.

FIGS. 1 and 2 show an orthopedic device in the form of a patellofemoral support according to a first embodiment of the disclosure, with a perspective view of opposed sides of the patellofemoral support offered by both FIGS. 1 and 2, respectively. The patellofemoral support 100 may comprise a sleeve 102 arranged to surround at least a portion of a leg of a user. The sleeve 102 may be formed from a continuous compressive knit ensuring dynamic fit, comfort, and breathability. The continuous compressive knit may comprise multiple discrete sections of material having different properties corresponding to different portions of the limb, as described in U.S. Patent Publication no. 2018/0078398, published Mar. 22, 2018.

For instance, donning and doffing of the sleeve, breathability, and functionality may be enhanced by providing regions having different densities, elasticities, and other features. The sleeve 102 is not limited to a compressive sleeve but may alternatively be formed of any suitable material for surrounding a limb, such as elasticized material or elastic or inelastic material as is known in the orthopedic arts. The sleeve 102 may comprise features to aid donning, doffing, and retaining the sleeve 102 on the limb of a user, such as fold-down portions and pull tabs similar to the above disclosure.

The sleeve 102 may support a buttress 103 which is arranged to align, stabilize, cushion and/or protect a patella of the user. The buttress 103 may be formed from an elastomeric, thermoplastic, or viscoelastic material, or any other suitable material, and may be supported over, under, and/or within a body or thickness of the sleeve 102. The sleeve 102 has first and second strap assemblies 104, 106, which connect to and extend from a portion of the sleeve 102 and extend around a portion of the sleeve 102. In the embodiment, the buttress 103 is shown as extending above or proximal relative to the patella, but it will be understood that the buttress 103 may comprise any suitable configuration relative to the user's limb and the patellofemoral support 100.

In the depicted embodiment, the first and second strap assemblies 104, 106 are arranged to extend from a medial or a lateral side of the patellofemoral support 100, as would be defined by a sagittal plane, respectively, of the sleeve 102, and to connect to an opposite side of the patellofemoral support 100. The first and second strap assemblies 104, 106 preferably overlap at a predetermined portion of the patellofemoral support 100 to apply forces to a portion of the limb, particularly the patella.

The first and second strap assemblies 104, 106 may have a tapering configuration, as in the embodiment of FIGS. 1 and 2, with a wider configuration at a first end originating at the sleeve 102, and a narrower configuration at a second end removably attaching at the opposite side of the sleeve 102 at a predetermined location. The strap assemblies 104, 106 may define a predetermined length arranged to cooperate with the sleeve 102 to provide optimal amounts of force to the patella or at other parts of the limb. The strap assemblies 104, 106 may be configured for providing user-specific support, such as by adapting to the specific dimensions of a user. The strap assemblies 104, 106 may comprise any suitable material, including but not limited to textiles, polymeric materials, or otherwise.

The strap assemblies 104, 106 may originate at their first ends at a same height or place on their corresponding medial or lateral sides, relative to an axis X-X of the sleeve 102. Alternatively, the strap assemblies 104, 106 may be located at different locations relative to the axis X-X, to incur more or less tensioning and corresponding compression of the buttress 103 depending on the area of the patella experiencing pain or requiring immobilization and/or stabilization. This arrangement may be particularly beneficial in a side-specific patellofemoral support, for example.

The tapering configuration of the first and second strap assemblies 104, 106 may advantageously distribute forces over the limb in a more comfortable manner, especially during flexion of the knee, and may provide proper pressure against a patella by supporting the sides and bottom of the patella. In this manner, the strap assemblies 104, 106 may cooperate with the buttress 103 to provide optimal support to the patella, with greater compression applied at particular portions of the patella. The strap assemblies 104, 106 may also facilitate donning of the patellofemoral support 100 by providing intuitive, symmetric attachment mechanisms. The strap assembles 104, 106 may be arranged to extend helically, that is in a generally spiraling configuration, around the patellofemoral support 100, such that the strap assemblies 104, 106 originate and terminate on the patellofemoral support 100 at different heights relative to the axis X-X. The strap assemblies 104, 106 may be arranged to extend, whether helically or circumferentially, only over an anterior portion A of the patellofemoral device 100.

The patellofemoral support 100 may comprise a buttress 108 arranged to extend distally of and around at least a portion of the patella on an anterior side A of the patellofemoral support 100. The buttress 108 may be provided in complement to or instead of the buttress 103. The buttress 108 may impart greater rigidity to the patellofemoral support 100 than the compressive sleeve 102, with extending portions that cooperate with the sleeve 102 and the first and second strap assemblies 104, 106 to apply forces to the patella in predetermined directions and at predetermined portions of the patella. The buttress 104 may be arranged within a thickness of the sleeve 102, or may extend either over or under the sleeve 102.

For example, an extending portion of the buttress 108 may be arranged to extend over the patellar tendon of the user. As the first and second strap assemblies 104, 106 are fastened, the strap assemblies 104, 106 may press inwardly upon the extending portion of the buttress 108 to apply pressure to the patellar tendon and thereby relieve pain, inflammation, and other sources of discomfort as well as supporting the apex of the patella. Additionally, or alternatively, an extending portion of the buttress 108 may be arranged to extend proximally around a side of the patella, thereby imparting forces to a side of the patella as the strap assemblies 104, 106 are fastened. This may be particularly advantageous for users suffering from patellar tracking in a particular direction, as the forces imparted by the first and second strap assemblies 104, 106 and the buttress 108 are arranged to stabilize and/or immobilize the patella, reducing pain and improving comfort for a user.

The patellofemoral support 100 may further comprise rigid or semi-rigid first and second stays 126, 128 arranged in or on the sleeve 102 within first and second stay panels 110, 112, respectively. The stay panels 110, 112 may retain the stays 126, 128 in position relative to the sleeve 102. The first and second stays 126, 128 may be arranged on opposed medial and lateral sides of the patellofemoral support 100 and may comprise a hinge portion facilitating flexion and extension of the leg. The hinges may be formed in the manner of U.S. patent application Ser. No. 16/058,024, filed Aug. 8, 2018.

The first and second stay panels 110, 112 may additionally define a structurally sound surface for supporting the first and second strap assemblies 104, 106 as pressure or forces are applied to the patella. The first strap assembly 104 may comprise a first main strap 113 connected to and extending from an anterior portion or side of the first stay panel 110. The first main strap 113 may extend across the anterior side A of the patellofemoral support 100 and attach via a first strap end 114 to the opposite side of the patellofemoral support 100. Likewise, and subsequently or simultaneously, a second main strap 115 of the second strap assembly 106 may be connected to and extend from an anterior portion of the second stay panel 112, overlapping the first strap assembly 104 as it extends across the anterior side A toward the opposite side of the patellofemoral support 100, terminating in and attaching by means of a second strap end 116. The first and second strap assemblies 104, 106 may extend symmetrically or asymmetrically and may comprise different shapes, lengths, or materials as suitable. The depicted arrangement is merely exemplary and the second main strap 115 may be secured beneath the first main strap 113.

The first and second strap ends 114, 116 may comprise first and second strap tabs 118, 120, respectively. The strap tabs 118, 120 may each define a reinforced end portion bearing a fastener arranged for attaching to a portion of the compressive sleeve 102 or the patellofemoral support 100. In the depicted embodiment, the first and second strap tabs 118, 120 comprise hook-and-loop-type fastener material, arranged for engaging with a corresponding hook-and-loop type fastener material provided on first and second tab landing areas 132, 142, respectively. The landing areas 132, 142 may be formed as extensions of the first and second stay panels 110, 112. Alternatively, the first and second stay panels 110, 112 may be entirely formed of hook-and-loop-compatible material, allowing the tabs 118, 120 to attach anywhere along the length of the stay panels 110, 112. Discrete regions or an entirety of the sleeve 102 may comprise or be formed of material compatible with the fastener material of the strap tabs 118, 120.

By anchoring the first and second strap assemblies 104, 106 on the first and second stay panels 110, 112 at first and/or second end of the strap assemblies 104, 106, the first and second strap assemblies 104, 106 may impart necessary forces to the knee owing to the structural soundness of the first and second stays 126, 128. This advantageously may facilitate effective forces to be applied around the user's limb and without extending around a posterior portion or side P of the patellofemoral support 100. This reduces the complications and discomfort associated with or caused by posteriorly extending straps, particularly during flexion and extension, as well as when the user or sitting or lying down.

The first and second stay panels 110, 112 may define first and second gaps 136, 140, respectively, between a main portion of the stay panels 110, 112 and first and second panel transition portions 130, 138. The gaps 136, 140 may separate the first and second panel transition portions 130, 138 from the main portions of the stay panels 110, 112, allowing for greater flexibility and ease of use as the first and second strap assemblies 104, 106 which depend therefrom are wrapped around the anterior side A of the patellofemoral support 100. The gaps 136, 140 may be formed proximate first and second hinge areas 134, 135 of the first and second stays 126, 128, respectively, or may be located at any suitable location along the stay panels 110, 112.

The sleeve 102 may define first and second anti-connection portions 122, 124 proximate the first and second landing areas 132, 142. The anti-connection portions 122, 124 may be arranged to not connect to the fastener or fastener material borne by the first and second strap tabs 118, 120. For example, the anti-connection portions 122, 124 may be formed from a material that does not cooperate with hook-and-loop-type fasteners. By providing the first and second anti-connection portions 122, 124, misplacement of the first and second tabs 118, 120 is prevented, as is damage to the material forming the sleeve 102, such as by contact with the hook portions of hook-and-loop-type fastener borne by the tabs 118, 120. Compliant and longer-term use of the patellofemoral support 100 is thereby facilitated.

FIG. 1A depicts a variation of the patellofemoral support 100 of FIGS. 1 and 2. The patellofemoral support 101 has a sleeve 102a and first and second strap assemblies 111a, 111b. While the first and second strap assemblies 111a, 111b intersect over a buttress 108, each of the first and second strap assemblies 111a, 111b each comprises first and second straps 117a, 119a, 117b, 119b.

Taking the first strap assembly 111a as an example, the first strap 117a extends from generally proximal or at the proximal side of a knee center Kc relative to an axis X-X of the support 101, whereas the second strap 117b extends from generally distal or at a distal side of the knee center Kc. Each of the first and second straps 117a, 117b extends from the medial side M, by way of example, of the sleeve 102a. The first and second straps 117a, 117b may converge at an intersection or convergence 125 over the lateral side L of the sleeve 102a, with one of the first and second straps 117a, 117b extending over the other at the convergence 125 to a shared tab 127. The first and second straps 117a, 117b may be separated along the medial side M by a distance or clearance D1, and may or may not have a same width.

In like manner, the first and second straps 119a, 119b of the second strap assembly 111b may extend laterally to medially and may have a predetermined configuration for providing a convergence or otherwise interacting for applying appropriate forces to the user. As described previously, the first and second strap assemblies 111a, 111b may be arranged to extend from and be anchored by first and second stay panels 110a, 112a.

In any of the embodiments described herein, the strap assemblies may be segmented into at least two straps as in FIG. 1A to approximate the shape of the strap assemblies depicted as comprising a single strap. Moreover, depending on the patella pain or issue, the strap assemblies and buttress shapes are not limited to their placement in the depicted embodiments, but rather may be interchanged according to whether greater support is required on one or both of the medial or lateral sides of a user's knee. For example, a first strap assembly bifurcated or segmented into two straps may extend laterally to medially for gripping a patella over a greater surface area on the lateral side, while a second strap assembly extending medially to laterally may have a non-segmented configuration and accordingly may extend over less surface area.

Figures 3, 4:
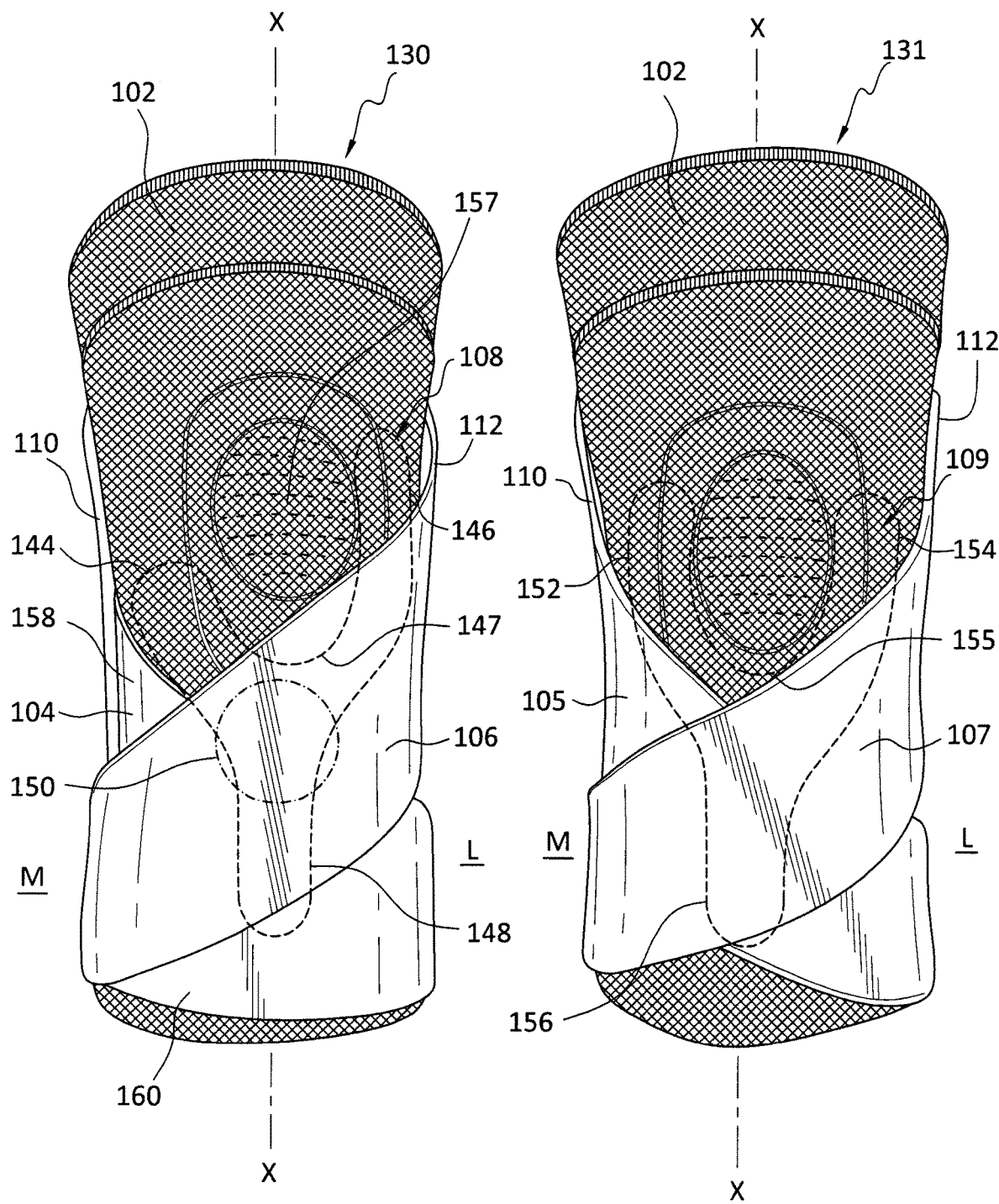
FIG. 3 is a front elevational view of a patellofemoral support according to another embodiment of the disclosure.
FIG. 4 is a front elevational view of a patellofemoral support according to another embodiment of the disclosure.

FIGS. 3 and 4 depict variations of patellofemoral supports 130, 131. In both FIGS. 3 and 4, the patellofemoral supports 130, 131 may comprise the sleeve 102 and the first and second stay panels 110, 112 of the patellofemoral support 100. The sleeve 102 may comprise a knee area 157, which may comprise material with greater flexibility and/or breathability than other portions of the sleeve 102, such that as the leg flexes and extends, the patella is accommodated and/or stabilized or immobilized by the sleeve 102 without excessive downward pressure on the patella.

The patellofemoral supports 130, 131 in FIGS. 3 and 4 may comprise buttresses 108, 109, respectively. The buttresses 108, 109 may advantageously comprise a rigid or semi-rigid material for applying forces to the patella or surrounding tissue, yet may be sufficiently pliant to resiliently deform in predetermined directions as the leg flexes and extends, thereby retaining their position relative to the sleeve 102 and providing continuous pressure to the patella. The buttresses 108, 109 may be formed of any suitable material.

In FIG. 3, the buttress 108 comprises first and second buttress arms 144, 146 extending from a buttress dip 147 and extending around medial and lateral sides M, L of the patella. The second buttress arm 146 may extend proximally on the patellofemoral support 130 a greater distance than the first buttress arm 144, such that the second buttress arm 146 abuts a substantial entirety of the corresponding side of the patella, whereas the first buttress arm 144 abuts only a portion of the corresponding opposite side of the patella, such as one quarter, one third, one half, or otherwise. The buttress dip 147 may be configured to define an inner curvature corresponding to a general shape of a patella and to abut a bottom side or portion of the patella. By contrast, the buttress arms 144, 146 may be arranged symmetrically around the patella. The buttress 108 is not limited to the depicted configuration, but may adopt any suitable configuration.

A buttress extension 148 may depend distally from the buttress dip 147 to extend over a patellar tendon of a user as the first and second buttress arms 144, 146 extend around sides of the patella. As first and second strap assemblies 104, 106 in FIG. 3 are fastened, the first and second strap assemblies 104, 106 may define an intersection 150 that may be arranged to press upon the buttress 108. The intersection 150 may extend over the buttress extension 148 to press the buttress extension 148 against the patellar tendon, providing stability and relieving pain and inflammation thereof. The first and second strap assemblies 104, 106 may be configured such that the intersection 150 extends over a substantial entirety of the buttress extension 148, the buttress dip 147, the first and second buttress arms 144, 146, or combinations thereof.

The first and second strap assemblies 104, 106 may be arranged to press the first and second buttress arms 144, 146 in toward the leg as well as to press the patella toward a central position; that is, in an embodiment the first buttress arm 144 may press the patella in a lateral direction L, while the second buttress arm 146 may press the patella in a medial direction M. Because of the asymmetry of the first and second buttress arms 144, 146, the second buttress arm 146, pressed by the second strap assembly 106 and applying forces to the patella, may press the patella further in the medial direction M or with greater force than the first buttress arm 144 presses the patella in the lateral direction L in the patellofemoral support 130.

The first strap assembly 104 is asymmetric relative to the second strap assembly 106 in that it presses down on the patella tendon, providing compression for anti-inflammatory and pain relief. As depicted, the first strap assembly 104 extends from a location distally relative to the second strap assembly 106, and has a wider shape in that a first portion 158, more proximal than a second portion 160, extends generally helically from the medial side M to the lateral side L relative to the axis X-X. The second portion 160 extends generally circumferentially about the sleeve 102 and axis X-X toward the lateral side L. As a variation, the first strap assembly 104 may comprise at least two straps, as in FIG. 1A, approximating the first and second portions 158, 160. This strap assembly exemplifies how any of the strap assemblies depicted herein may have tapering widths or directionally differing portions.

The second strap assembly 106 may be located proximally relative to the first strap assembly 104 on the lateral side L and relative to the axis X-X. The second strap assembly 106 may extend over a large portion of the buttress 108 and corresponding buttress arm 146 to offer more compression on the lateral side L.

This arrangement may be particularly advantageous for users whose patella tracks to a particular side, especially as the knee bends in flexion. The first and second strap assemblies 104, 106 advantageously retain the buttress 108 in its desired configuration even as the user's leg moves, overcoming a significant advantage of existing devices which have highly dynamic configurations throughout a range of user movements, leading to inconsistent support.

In the embodiment of FIG. 4, the buttress 109 may comprise equally or substantially symmetrically dimensioned first and second buttress arms 152, 154, connected at a buttress dip 155 and connected to a buttress extension 156. As in the embodiment of FIG. 3, the buttress arms 152, 154 may be arranged to extend around opposed sides of a patella and to impart forces thereto as a result of the first and second strap assemblies 105, 107. The symmetrical arrangement of FIG. 4 may be appropriate for a user with patella pathologies that are not asymmetric or involve the patella tracking to a particular side. Rather the embodiment of FIG. 4 may provide symmetric and effective stabilization on both medial and lateral sides M, L of the patella.

The configuration of the first and second strap assemblies 105, 107 with the symmetric configuration of the buttress 109 allows for intuitive, accurate, and effective bracing of the knee and the patella in particular by a user, as proper donning of the patellofemoral support 131 is facilitated by the complementary shapes of the first and second strap assemblies 105, 107 relative to the shape of the buttress 109. As a user dons the patellofemoral support 131, the first and second strap assemblies 105, 107 may be easily and accurately applied over the sleeve 102, with the tapering shape of the strap assemblies 105, 107 corresponding to the shape of the patella and the buttress 109 and comfortably abutting thereagainst.

The first and second strap assemblies 105, 107 may be each arranged as two or more substraps of equal length and being joined at first and second ends thereof to form a single composite strap assembly, with the two or more substraps of each single composite strap assembly facilitating greater flexibility of the strap assemblies 105, 107 to conform to a user's dimensions and increasing durability as shown in FIG. 1A. In an embodiment, the two or more substraps may substantially overlap at a first end and may separate at a second end, such that the two or more substraps diverge towards the second end. The dimensions and properties of the buttresses 108, 109, including the buttress arms 144, 146, 152, 154 and the buttress extensions 148, 156, as well as the configuration and constructions of the strap assemblies 104, 106, 105, 107, may be arranged in any suitable configuration for applying desired forces, support, or immobilization to a limb.

Figure 5:
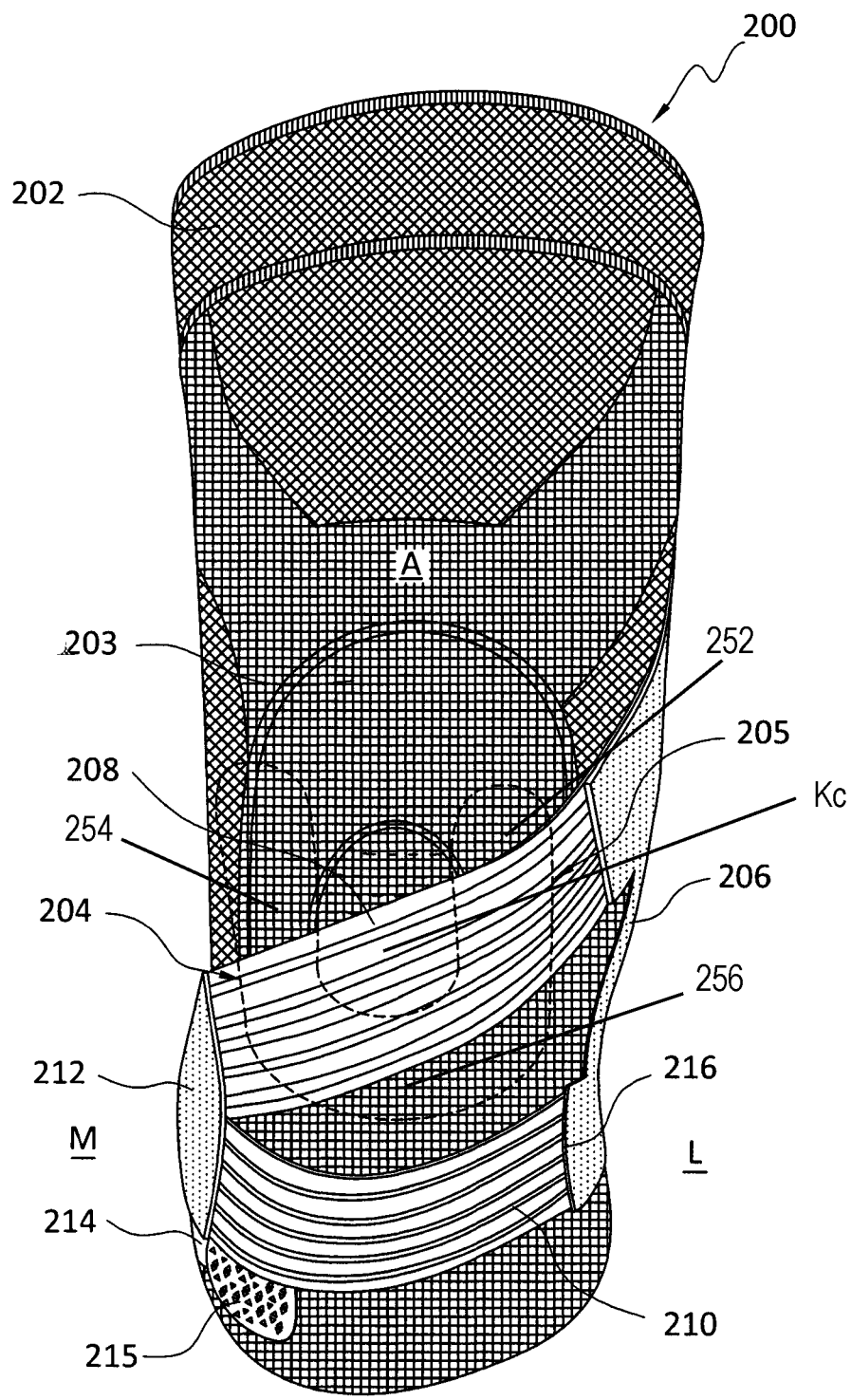
FIG. 5 is a front elevational view of a patellofemoral support according to another embodiment of the disclosure.

Another embodiment of a patellofemoral support 200 according to the disclosure is shown in elevational view in FIG. 5. The patellofemoral support 200 may comprise a sleeve 202 and may be formed from any suitable material as discussed in previous embodiments. The sleeve 202 may define discrete regions having different properties appropriate for the particular portion of the user's limb to which the regions correspond.

The patellofemoral support 200 may comprise a buttress 203 proximate a buttress 205. Both the buttress 203 and the buttress 205 may be connected to and/or contained entirely within, over, or under a thickness of the sleeve 202 and are shown schematically. The buttress 205 may define an O-, U- or Y-shape or any other configuration suitable for surrounding a user's patella on lateral, medial, proximal, and/or distal sides or portions thereof.

The patellofemoral support 200 may comprise a strap system 204 including a helical or diagonal strap 208 and an anterior circumferential strap 210. The helical strap 208 and the anterior circumferential strap 210 may be arranged to extend from a first side of the sleeve 202 and to pass over an anterior side A of the patellofemoral support 200. The straps 208, 210 may removably connect to a second side of the sleeve 202 by an appropriate fastener, such as a hook-and-loop type fastener or any other suitable fastener.

The anterior circumferential strap 210 is depicted as extending distally of the helical strap 208, but it will be understood that the anterior circumferential strap 210 may extend in any relationship with the helical strap 208, including proximally. As in previous embodiments, the helical strap 208 and anterior circumferential strap 210 may, by extending substantially only anteriorly, advantageously reduce complications and interference by the straps 208, 210 with flexion and extension on a posterior side of the patellofemoral support 200.

The strap system 204 may be arranged to connect to and extend from the first side of the sleeve 202 at a first stay panel 206, which may be arranged on a medial or lateral side of the patellofemoral support 200 and whereat a strut or hinge may be arranged as detailed in previous embodiments, particularly depending on a user's needs. For a user with patella pathologies requiring forces pressing primarily medially to laterally, a first configuration may be suitable, whereas for a user requiring forces pressing primarily laterally to medially, a second configuration may be suitable. The anterior circumferential strap 210 may comprise a circumferential strap attachment 216 configured to attach to the first stay panel 206 on the lateral side L, imparting desired flexibility to facilitate intuitive, effective, and easy donning of the support 200.

In the embodiment of FIG. 5, the strap system 204 may be arranged to extend over the buttress 205 asymmetrically; that is, the helical strap 208 may extend over a greater proportion of a first or lateral branch 252 of the buttress 205 relative to a second or medial branch 254 of the buttress 205, such that the first and second branches 252, 254 extend from opposed sides of a base 256 of the buttress 205, which is distal of the knee center Kc, as also depicted and defined in FIG. 1A. In this manner, the helical strap 208 may be arranged to press and exert forces upon the buttress 205 in an overall lateral-to-medial fashion, assisting a user suffering from a patella that tracks in the medial-to-lateral direction.

To ease the process of properly donning the patellofemoral support 200, the strap system 204 may be provided with a strap tab 212 arranged to join the helical strap 208 and the anterior circumferential strap 210 at a single second or free end. A tab landing area 214 may be defined by or on the sleeve 202 and may correspond to a predetermined location for attaching the strap tab 212. As in the embodiments described in FIGS. 1-4, an anti-attachment section 215 may be defined proximate the tab landing area 214 to prevent the strap tab 212 or fasteners arranged thereon from contacting, gripping, and/or damaging the material forming the sleeve 202 or from attaching the strap system 204 in an improper or suboptimal configuration. The anti-attachment section 215 may further be arranged to aid a user in donning the patellofemoral support 200 by urging the user to place the strap tab 212 at a location that may ensure that optimal and/or effective forces are applied.

The tab landing area 214 may be formed by or on a second stay panel 207 (shown in FIG. 6) located on an opposite side from the first stay panel 206. The tab landing area 214 may have a shape or configuration closely corresponding to a shape, size, or configuration of the strap tab 212, or may have a larger configuration or shape than the strap tab 212, thereby facilitating a plurality of possible configurations of the strap system 204 based on an individual's needs. For instance, the tab landing area 214 may extend a predetermined distance up the second stay panel 207 to allow the strap system 204 to have a plurality of vertical orientations depending on the user's particular needs, which may vary during the course of use or recovery.

Figures 6, 7:
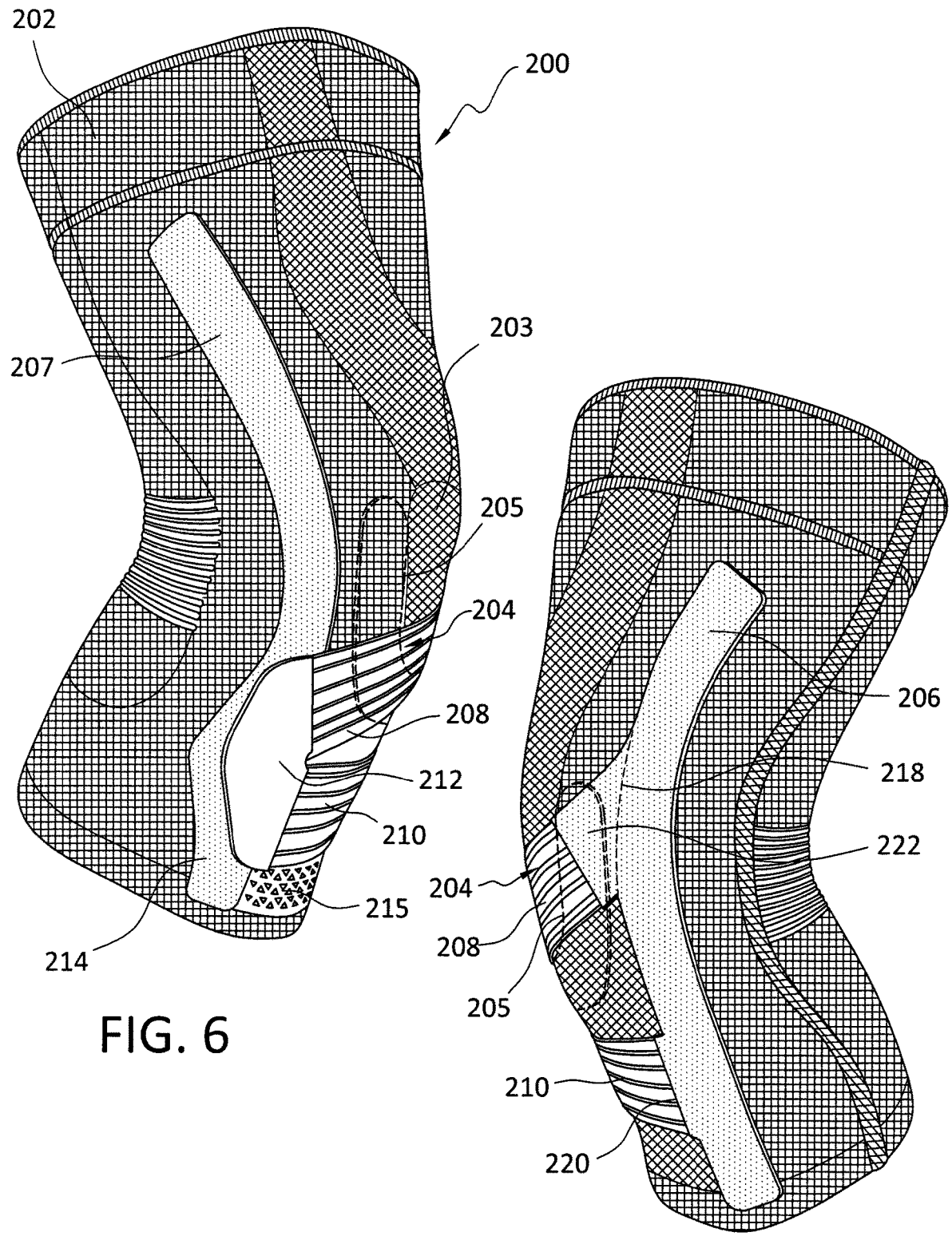
FIG. 6 is a side elevational view of the embodiment of FIG. 5.
FIG. 7 is a side elevational view of the embodiment of FIG. 5.

In the side elevational view of FIGS. 6 and 7, the orientation of the strap system 204, the buttress 205, and the sleeve 202 can be seen in greater detail. The second stay panel 207 may define a configuration that is complementary to a shape of the strap tab 212 at predetermined locations. The anti-attachment section 215 is shown extending anteriorly relative to the second stay panel 207, but it will be understood that the anti-attachment section 215 is not limited to this configuration and may extend in any suitable configuration relative to the sleeve 202. A plurality of tab landing areas and/or anti-attachment sections may be provided in any number, shape, or configuration as suitable. It will be understood that the tab landing area 214 and the anti-attachment section 215 may comprise any suitable arrangement relative to each other.

As seen in FIG. 7, the strap system 204 may comprise first and second strap interfaces 218 and 220 arranged to correspond to the helical strap 208 and the anterior circumferential strap 210, respectively. The strap interfaces 218, 220 may be arranged to connect the helical and anterior circumferential straps 208, 210 to the first stay panel 206, thereby anchoring the strap system 204 relative to the sleeve 202 and facilitating the forces applied by the strap system 204 to the patella and the limb. An extension 222 may extend between the first strap interface 218 and the helical strap 208, and may comprise flexible, elastic, or other properties suitable for helping a user to help position the helical strap 208 at an optimal location relative to the patella.

Figures 8, 9:
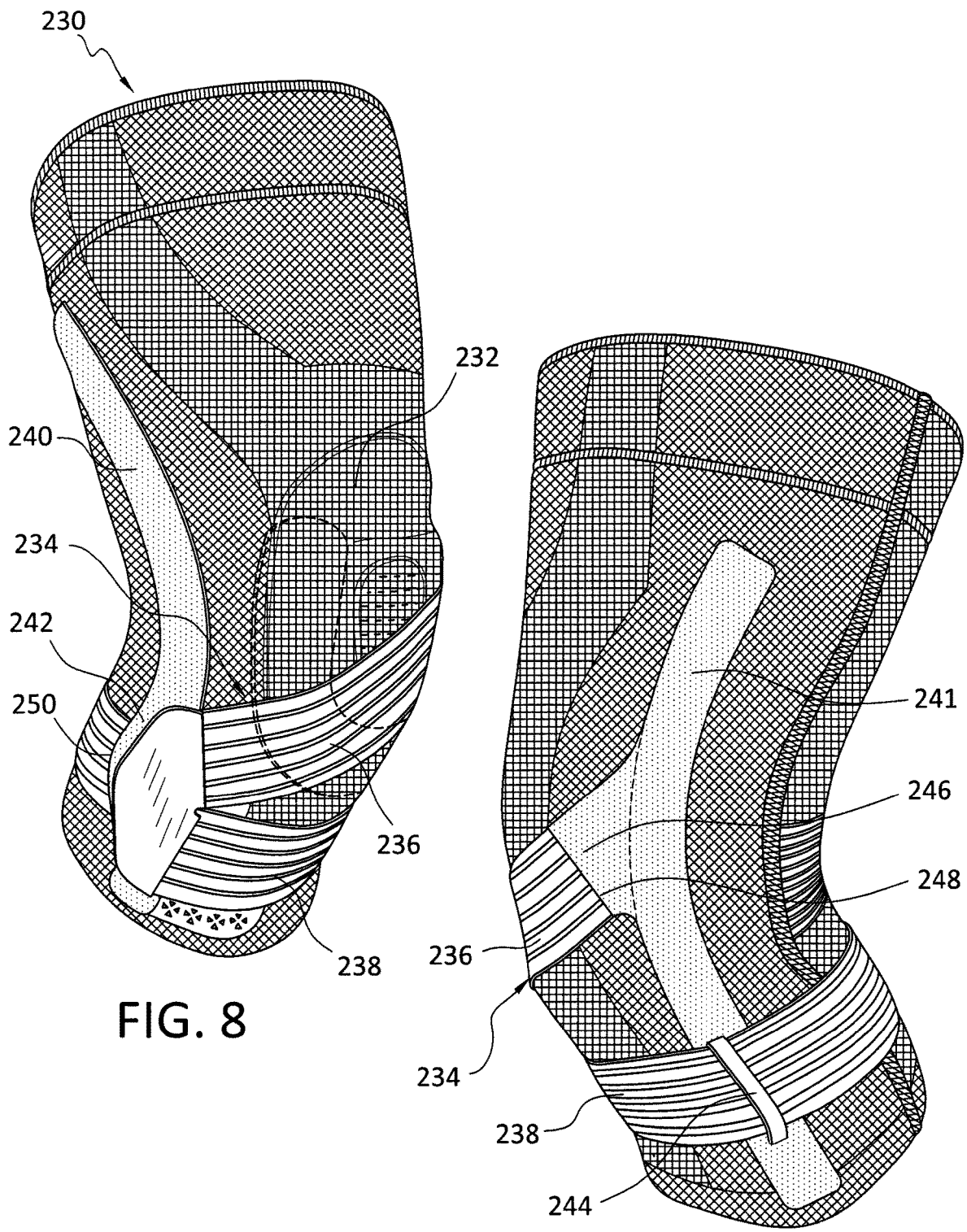
FIG. 8 is a side perspective view of a variation of the embodiment of FIG. 5.
FIG. 9 is a side perspective view of the embodiment of FIG. 8.

In an alternative embodiment depicted in FIGS. 8 and 9, a patellofemoral support 230 may comprise a knee sleeve or support 232 and a strap system 234. A buttress may be arranged to extend over, below, or within a thickness of the sleeve 232 of the patellofemoral support 230 and, like the embodiments of FIGS. 5-7, may be arranged with at least first and second branches extending at least distally of and around first and second sides of the patella. The strap system 234 may comprise a helical strap 236 and an anterior circumferential strap 238 configured with a strap tab joining the helical and anterior circumferential straps 236, 238 at a single free or second end to facilitate accurate and intuitive donning. The strap tab may comprise a fastener arranged to connect to a tab landing 242 defined by or on a first stay panel 240. The first stay panel 240 may further comprise a stay or hinge as discussed previously.

The strap system 234 may extend from a second stay panel 241 arranged at an opposite side of the patellofemoral support 230. The second stay panel 241 may comprise a stay or hinge, which may have added rigidity relative to the sleeve or straps to facilitate applying forces through the strap system 234. The second stay panel 241 may attach to the helical strap 236 at an extension 246, the extension 246 facilitating flexibility to allow the helical strap 236 to extend over the patella at an optimal location based on a user's dimensions and needs. A strap interface 248 may extend from the extension 246 to connect to the helical strap 236.

A loop 244 may be defined by or proximate the second stay panel 241 and may be arranged to cooperate with the anterior circumferential strap 238. To stabilize the patellofemoral support 230 around the leg of the user, the anterior circumferential strap 238 may be arranged to extend around a substantial entirety of the patellofemoral support 230, thereby better distributing the forces applied by and through the strap system 234 and the patellofemoral support 230. This prevents twisting or other undesired migrations of the patellofemoral support 230 relative to the leg as a result of tensioning or applying forces through the strap system 234.

The anterior circumferential strap 238 may extend through the loop 244 over the second stay panel 241 from an origin at the first stay panel 240. A strap interface 250 may extend from the first stay panel 240 to connect to a first end of the anterior circumferential strap 238, as seen in FIG. 8. By providing the anterior circumferential strap 238 of the embodiment of FIGS. 8 and 9, the problem of tensioning components of patellofemoral supports leading to unwanted migration or twisting of the patellofemoral support is addressed. As in previous embodiments, the anterior circumferential strap 238 may be arranged in any suitable configuration relative to the helical strap, including proximally.

FIGS. 10-12 illustrate another embodiment of a patellofemoral support 300 according to the disclosure. The patellofemoral support 300 may comprise a buttress 301 arranged to be applied against a patella of a user by a strap assembly 306. A sleeve 302 may be arranged with an opening 304 configured to receive and hold a patella of a user, with the strap assembly 306 configured to press the buttress 301 against a portion of the patella. At least one hinge 316 may be formed along a medial and/or lateral side of the patellofemoral support 300.

The strap assembly 306 may extend from the sleeve 302 at an elastic portion 310 and may comprise first and second strap segments 312, 314. The first and second strap segments 312, 314 may be arranged to extend in a generally circumferential fashion proximally or above and distally or below the opening 304, respectively. The opening 304 may be bounded by an opening edging 322 configured to provide cushioning and retention of the patella. The opening edging 322 of the sleeve 302 may comprise foam, padding, reinforcement sections, or other features that enhance comfort and patella retention around the opening 304 by resisting outward movement of the patella.

The sleeve 302 may be formed as in previous embodiments of any suitable material. In an embodiment, the sleeve 302 may be formed from a soft and/or compressive material configured to provide comfort to a user and to facilitate intuitive and easy donning of the patellofemoral support 300. The sleeve 302 may be a continuous sleeve and may define first and second strap landing portions 318, 320 configured to cooperate with corresponding fasteners of the first and second strap segments 312, 314, respectively. The first and second strap landing portions 318, 320 may be formed on a region of the sleeve 302 near the at least one hinge 316, facilitating a circumferential or near-circumferential arrangement of the first and second strap segments 312, 314 when attached to the strap landing portions 318, 320 and ensuring attachment of the strap segments at a structurally secure region of the support 300. The near-circumferential or circumferential arrangement may advantageously secure the straps 312, 314 without undesired torqueing of the limb and/or the patellofemoral support 300 or twisting and migration of the support 300 relative to the limb.

FIG. 11 depicts the embodiment of FIG. 10 in greater detail. The buttress 301 may comprise a curved buttress profile 323 arranged for complementing or corresponding to a natural shape of the patella. The buttress 301 may further comprise first and second sections 324, 326 defining the buttress profile 323. The first section 324 may be a raised portion by having a greater height than the second section 326 and may extend from a surface of the second section 326. The buttress 301 may connect to a strap base 328 from which the first and second strap segments 312, 314 extend and which may connect to the elastic portion 310. The first and second sections 324, 326 may be configured to provide optimal pressure both laterally (e.g. by pressing against a side of the patella) and vertically (e.g. by pressing downward or inward upon a portion of the patella). The buttress 301 is not limited to this configuration but may comprise any suitable configuration.

The first and second sections 324, 326 may cooperate with the strap assembly 306 as they are pressed against a patella as the strap assembly 306 is wrapped around the patellofemoral support 300. The strap assembly 306 may apply forces against the patella through the buttress 301 and retain the patella in a desired configuration, particularly as the user bends the leg in flexion or extension. Whereas the first section 324 may press down, the second section 326 may rather be configured to press inward from a lateral-to-medial direction owing to its broader, more shallow configuration. The buttress 301 may be formed of silicone, elastomeric material, or any other suitable material for providing forces without damaging the skin of the user, providing uncomfortable pressure points, or otherwise discomforting the user.

The elastic portion 310 may advantageously allow for the strap assembly 306 to be flexibly and accurately arranged relative to the patella, and may further allow for the strap assembly 306 to apply variable degrees of forces to the user and/or to correspond effectively to different dimensions of different users, or to a single user's potentially dynamic dimensions during recovery from an operation or injury, for example.

FIG. 12 depicts an alternative embodiment of the patellofemoral support of FIG. 10, comprising a dynamic strap embodiment. The patellofemoral support 300 of FIG. 12 comprises a strap assembly 306 having a strap base 328 and supporting a buttress having first and second portions 324, 326 as described in the embodiment of FIGS. 10 and 11.

The strap assembly 306 may advantageously comprise a strap base 328 connected to a strap extension portion 310. The strap extension portion 310 may be arranged to extend over a stay or stay panel 308 of the patellofemoral support 300, thereby securing or anchoring the strap assembly 306 on the patellofemoral support 300. This may aid the support 300 in applying effective forces to the limb repeatedly and without damaging the support 300.

The first and second strap segments 330, 332 may connect to first and second elasticized segments 334, 336, respectively, which may additionally connect to second strap segments 338, 340, respectively. The strap assembly 306 may terminate at first and second strap tabs 342, 344. The first and second strap tabs 342, 344 may support fasteners for removably connecting to the sleeve 302. The first and second strap segments 330, 332 and the second strap segments 338, 340, in contrast to the elasticized segments 334, 336, may be formed of material that is inelastic or substantially inelastic.

By providing a strap assembly 306 comprising elasticized segments 334, 336 between inelastic or substantially inelastic portions 330, 332, 338, 340, the strap assembly 306 may be more optimally or accurately conformed to the particular shape and size of a user, and appropriate levels of forces may be applied to the patella with reliable robustness of the straps. The elasticized segments 334, 336 may further aid in preventing unwanted twisting or migration of the patellofemoral support 300 by allowing the strap assembly 306 to extend around the user with reduced pulling and/or torqueing.

It is to be understood that additional elastic portions and inelastic portions may be defined by the strap assembly 306 and in alternative configurations, and the disclosure is not limited to the embodiment of FIG. 12. The strap assembly 306 is not limited to the embodiment shown in FIGS. 10-12, but may comprise any suitable configuration of straps and components, including fewer or more straps, helical, circumferential, or anterior- or posterior-only straps, or otherwise. The first and second strap segments may have a substantially similar configuration or may have different configurations as suitable.

Figure 13:
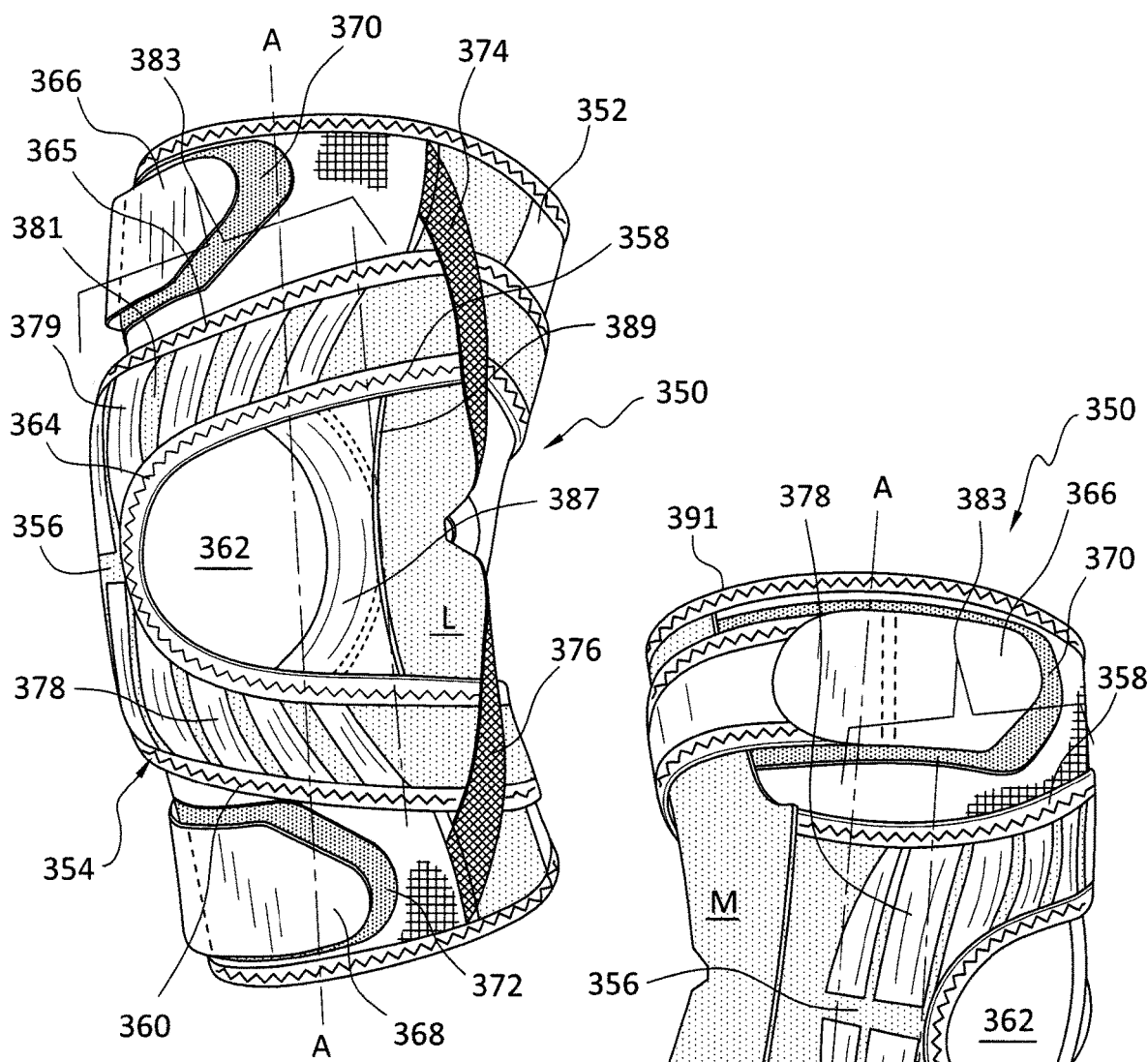
FIG. 13 is a first front perspective view of a variation of the patellofemoral support of FIG. 10.
Figure 14:
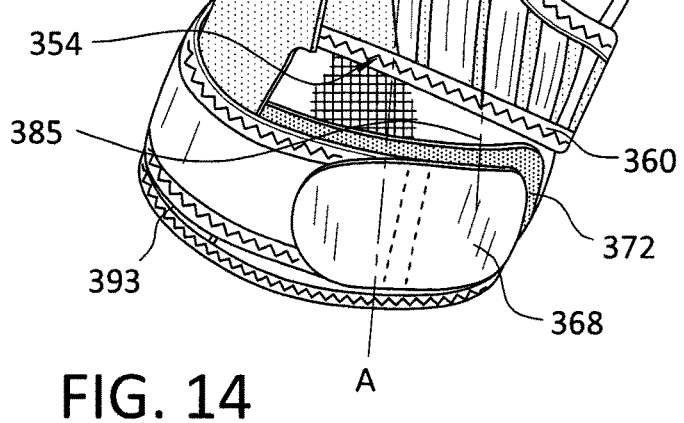
FIG. 14 is a second front perspective view of the patellofemoral support of FIG. 13.

FIGS. 13 and 14 illustrate another embodiment of a patellofemoral support 350 which is a variation of the patellofemoral support of FIG. 10. The support 350 includes a sleeve 352 having an opening 362, and a strap assembly 354. The strap assembly 354 has a first portion 356 hingedly secured to the sleeve 352, and a second portion having first and second straps 358, 360 extending from the first portion 356 to helically extend about the sleeve 352 and selectively secure thereto. The first and second straps 358, 360 extend about opposed sides of the opening 362. As shown in more detail in FIGS. 15 and 16, a patella buttress 380 is removably securable to an inner surface of the strap assembly 354 about a lateral or medial side L, M of the opening 362, to function similarly to the buttress in the embodiment of FIGS. 10-12.

The sleeve 352 preferably includes a padded ring 387 extending about the opening 362, as in preceding embodiments. For reference, the first and second sides of the opening 362 correspond to opposed sides of an axis A-A of the sleeve 352, bordered by first and second tangent lines 385, 389 on opposed sides of the opening 362, such as along the ring 387, and generally parallel to the axis A-A.

In the strap assembly 354, the first and second straps 358, 360 are arranged to extend about the thigh and calf, respectively. The sleeve 352 may be substantially uniform, as may be the first and second straps 358, 360. In this manner, the support 350 can be used to arrange the buttress 380 against either a lateral or medial side of the patella, and the support 350 is arranged for left or right knees, and either lateral or medial complications of the patella.

The second portion of the strap assembly 354 including the first and second straps 358, 360 is arranged to extend from the first portion 356 at a location corresponding to a first side of the opening 362. A length of a first side of the first portion 356 is secured to the sleeve 352 so the strap assembly 354 can be opened from the first side to better position the buttress 380 over or about an affected area of the user's patella. The first and second straps 358, 360 generally extend from the first portion 356 of the strap assembly 354 from a first line 385 generally tangent to a first side of the opening 362 and generally parallel to the axis A-A of the sleeve 350.

The support 350 includes at least one loop 374, 376 located on the sleeve 352 generally at a medial or lateral side of the sleeve 352. The at least one loop 374, 376 is arranged for at least one of the first and second straps 358, 360 to extend therethrough. The at least one loop 374, 376 extends obliquely relative to the axis A-A of the sleeve 352 to guide extension of at least one of the first and second straps 358, 360 about a periphery of the opening 362.

The loops 374, 376 are preferably on a side opposite the first portion 356 of the strap assembly 354 to better guide the first and second straps 358, 360 toward the peripheral edges of the sleeve 352. The loops 374, 376 also prevent migration of the first and second straps 358, 360 during use. The loops 374, 376 simplify the use and donning of the support 350 by preventing the straps 358, 360 from inadvertently migrating when donning and doffing the support 350. Indicia may be provided on the straps 358, 360 as a guide for donning or doffing, or for other means.

The first and second straps 358, 360 are arranged to extend from the first portion 356 of the strap assembly 354 circumferentially about the sleeve 352 to about the first portion 356 so a first end 366, 368 of the first and second straps 358, 360 removably secures to first and second landings 370, 372 on the sleeve 352. The first portion 356 extends from one of lateral or medial sides L, M of the sleeve 352 and at least one of the first and second straps 358, 360 generally helically extends toward a first or proximal edge 391 or a second or distal edge 393 of the sleeve 352, depending on the orientation of the sleeve 352.

The first and second straps 358, 360 extend to the proximal edge 391 or the distal edge 393 to provide a low profile and streamlined support, thereby removing excess material proximally or distally from where the straps 358, 360 secure. Also such an arrangement allows for a tighter-fitting brace as the straps 358, 360 extend to the periphery, either proximal or distal, of the support 350. The tighter-fitting brace facilitated by the arrangement of the first and second straps 358, 360 further ensures that unwanted migration or misorientation of the support 350 is achieved without effecting an undesirable tourniquet effect.

The first and second straps 358, 360 may extend nearly completely circumferentially about the sleeve 352, defined as at least 3000 about the sleeve 352 beginning from where the first or second strap 358, 360 extends from the first portion 356 and to the point whereat the first or second strap 358, 360 secures to the first or second landings 370, 372. Alternatively, the first and second straps 358, 360 may extend completely circumferentially about the sleeve 352, defined as at least 360° about the sleeve 352 beginning from where the first or second strap 358, 360 extends from the first portion 356 to the point whereat the first or second strap 358, 360 secures to the first or second landings 370, 372.

The first portion 356 may extend from an edge 353 of a medial M or lateral L side of the sleeve 352, and may extend from 5° to 60° about the sleeve 352. Regarding the circumferential extension of the first and second straps 358, 360, it is preferable that the first and second straps 358, 360 extend at least to the edge 353 or whereat the first or second landings 370, 372 begin to circumferentially extend about at least a segment of the sleeve 352. Preferably, the first and second landings 370, 372 intersect about the circumference of the sleeve 352 relative to the axis A-A. In this manner, the ends of the first and second straps 358, 360 will helically extend about the circumference of the sleeve and past or to the first portion 356, extending past the edge 353.

Figure 18:
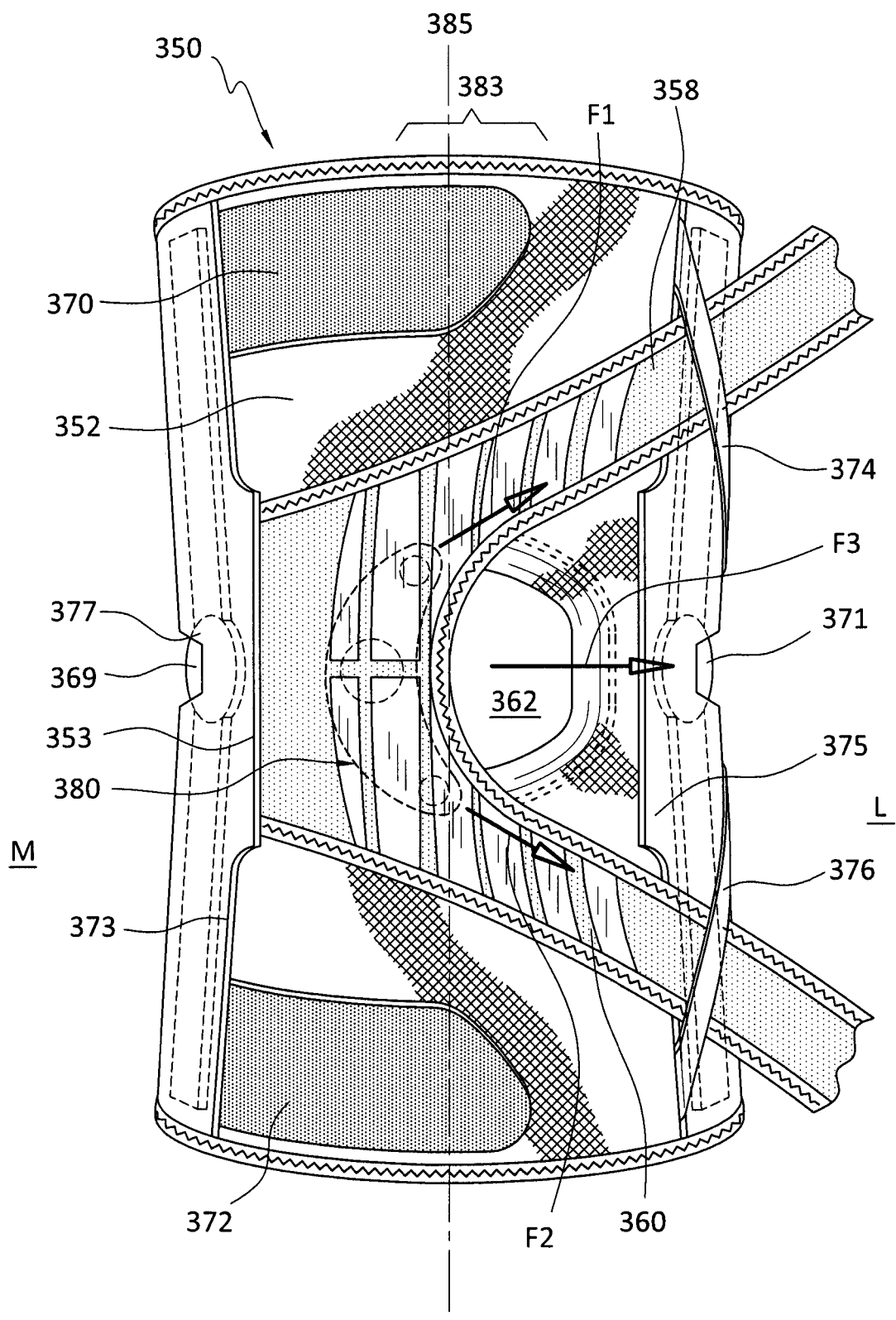
FIG. 18 is an elevational view of the patellofemoral support of FIG. 10.

FIG. 18 exemplifies how the sleeve 352 can have hinges 369, 371 located within sleeves 373, 375 located on medial and lateral sides of the support 350. The hinges 369, 371 are removable via openings 377 located along each of the sleeves 373, 375. A user may remove one or both hinges 369, 371. Each hinge 369, 371 includes first and second arms and an articulating portion connecting each of the first and second arms.

FIG. 18 illustrates how the buttress 380 may extend as the first and second straps 358, 360 are tensioned. Due to the tensioning of the first and second straps 358, 360, the buttress 380 may extend as well and pressure can be applied about the opening 362 to a user's patella. Such forces created F1, F2, F3 provide a compressive feel about the patella to provide better support to the user.

The first portion 356 is located between and spaced from the proximal and distal edges 391, 393 so the first ends 366, 368 are located between the first or proximal and second or distal edges 391, 393 and the first portion 356, respectively. The first and second landings 370, 372 are axially spaced besides the first portion 356, and may circumferentially extend in a segment corresponding to the first portion 356 and at least past the first line 385.

The strap assembly 354 may include a film 378 located on the first portion 356 and the first and second straps 358, 360. The film 378 may be located on either an outside surface and/or an inside surface of the strap assembly 354. The film 378 is arranged to inhibit stretching of the first and second straps 358, 360. The film 378 comprises a plurality of sections 379 spaced apart by clearances 381 along a segment of at least one of the first and second straps 358, 360 proximate a diameter of the opening 362.

The film 378 may be arranged in a geometrical configuration to encourage elasticity or flexibility of the first and second straps 358, 360 about the leg of the user. For example, in the depicted embodiment of FIGS. 13 and 14, the film 378 comprises a plurality of sections 379 spaced apart from one another and that are generally aligned with the axis A-A. In this manner, the first and second straps 358, 360 are able to circumferentially extend about the user's leg due to the clearances 381 between each individual section 379 of the film 378. Stretching of the first and second straps 358, 360 in an axial direction may be minimized due to the film 378.

The film 378 adds dynamic tensile properties, and may be further adapted for tensile properties according to the shapes of the sections 379 and clearances 381 therebetween. The sections 379 are not limited to being uniform in shape or size relative to one another, and there may be a higher density of sections 379 at one location as compared to another to increase or decrease relative tensile properties. The film 378 may limit or lock stretchability of the strap assembly 354 in a strategic location, such as about the opening 362. The film 378 reinforces the strap assembly 354 and may increase the durability and ruggedness in high-stress areas of the support 350.

As shown in FIGS. 13 and 14, the film 378 may extend about the first portion 356 of the strap assembly 354 on a first side of the opening 362, and the film 378 may extend along the first and second straps 358, 360 to a second side of the opening 362 proximate in length 383 to the padded ring 387. The film 378 may extend generally to the second line 389 so as to correspond to the opening 362, and may likewise extend along the first portion 356, which is displaced from the first line 385 sufficiently to accommodate the buttress 380. In one variation, the sections 379 of the film 378 may extend obliquely relative to peripheral first or inner and second or outer edges 364, 365 of at least one of the first and second straps 358, 360.

Figure 15:
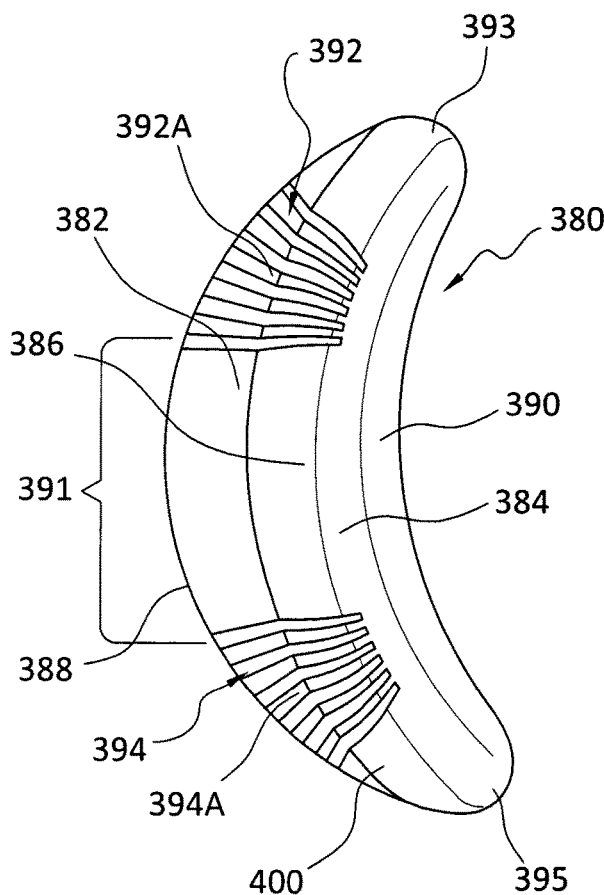
FIG. 15 is a front plan view of a buttress useable in a patellofemoral support.
Figure 16:
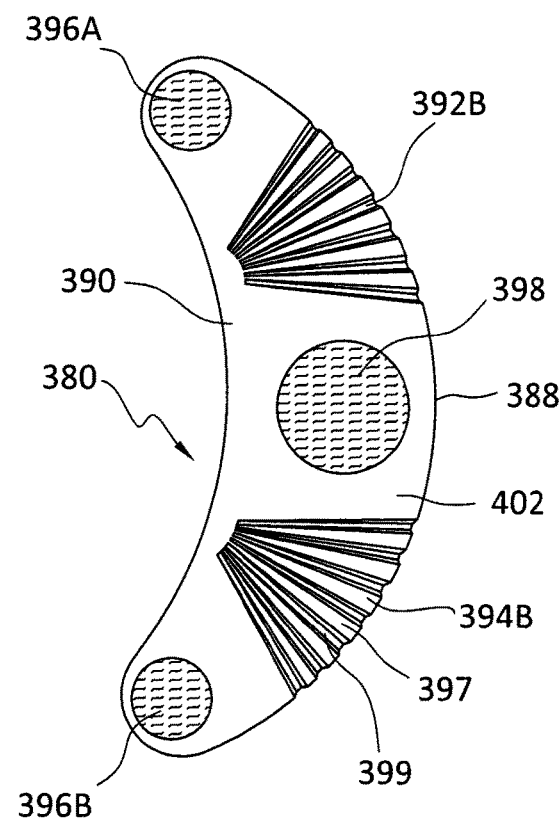
FIG. 16 is a rear plan view of the buttress of FIG. 15.
Figure 17:
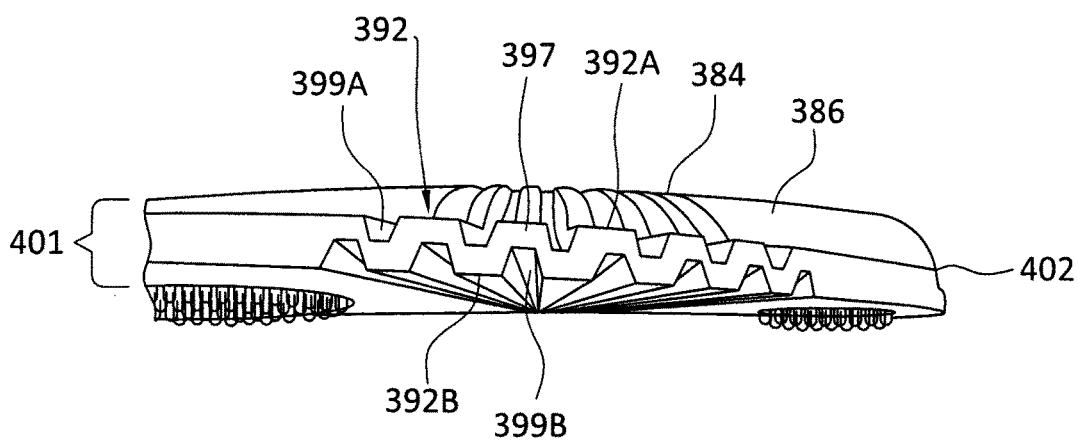
FIG. 17 is an elevational sectional view of the buttress of FIG. 15.

Referring to FIGS. 15-17, the buttress 380 may have an arcuate shape similar to the buttress in FIGS. 10-12, and may be constructed from a resilient material such as silicone, TPE (thermoplastic elastomer), and/or TPU (thermoplastic urethane such as thermoplastic polyurethane). The buttress 380 is arranged with a fastener system to offer a user the ability to slightly adjust the buttress 380 according to the user's individual anatomy. The buttress 380 includes adjustment features such as "accordion"-style ribs allowing a user to make slight and precise adjustments to the shape of the buttress 380. For example, while depicted in a basic arcuate shape, the flexibility of the material, in combination with the adjustment features, further in combination with the fastener system, allows a user to convert the buttress 380 into different shapes suitable for being applied against a patella. These shapes include a J- (straightening one end of the buttress), C- (adjusting both ends toward each other), I- (moving the ends away from each other to straighten the buttress), variations thereof, or any other suitable shape. When the user is done with the buttress 380 or removes it from the support 350, the inherent resilient nature of the material used to form the buttress 380 reverts to the generally arcuate shape, as depicted.

The buttress 380 may be arranged to removably secure to an inside surface of the first and second portions of the strap assembly 354, such as by hook-and-loop fastening. The buttress 380 forms first and second opposing peripheral edges 388, 390 having different radii. The buttress 380 defines a flat portion 382 having opposed flat surfaces along first and second sides 400, 402 of the buttress 380. The flat portion 382 generally corresponds to the first portion 365 of the strap assembly 354. The first peripheral edge 388 of the buttress 380 borders the flat portion 382. The second side 402 of the buttress 380 is substantially flat and adapted to secure to the strap assembly 354. The second side 402 of the buttress 380 includes at least one fastening element 396A, 396B, 398 adapted to removably engage the strap assembly 354. The fastening elements 396A, 396B, 398 may comprise hook material securable to loop material or the material forming the strap assembly 354.

The geometry of the buttress 380 is adapted to localized pressure about a patella when the strap assembly 354 is tensioned thereabout. A protruding portion 384 extends along the first side 400 of the buttress 380 and borders the second peripheral edge 390. A transitional portion 386 extends from the flat portion 382 to the protruding portion 384. The transitional portion 386 may have a rounded profile.

To ease bending of the buttress 380 and mitigate bunching of the buttress 380, the buttress 380 defines at least one series of ribs 392, 394 extending from the first peripheral edge 388 toward the second peripheral edge 390. The at least one series of ribs 392, 394 is formed from a thickness of at least the flat portion 388. The at least one series of ribs 392, 394 may extend along the first and second sides 400, 402 in alternating first and second rows 392A, 392B, 394A, 394B, respectively. The at least one series of ribs 392, 394 may extend to the protruding portion 384 along the transition portion 386 and generally extend in a converging orientation from the first peripheral edge 388 to the protruding portion 384.

The at least one series of ribs 392, 394 includes first and second series of ribs 392, 394 spaced apart by a middle section 391 of the buttress 380. Placing the at least one series of ribs 392, 394 facilitates bending of first and second end sections 393, 395 of the buttress 380 relative to the middle section 391. Each rib 397 may taper in width from the first peripheral edge 388 toward the protruding portion 384. Each clearance 399 between adjacent ribs 397 may taper according to a taper of the adjacent ribs 397, and may define a first set of clearances 399A on the first side 400 and a second set of clearances 399B on the second side 402. The first row of ribs 392A on the first side 400 may extend deeper into a thickness 401 of the buttress 380 than a second row of ribs 392B on the second side 402. The extent of a taper or extension toward the second peripheral edge 390 of the buttress 380 of each of the first and second ribs 392A, 392B, 394A, 394B may vary relative to one another. A depth of the clearances 399 may taper in depth or width as the second row of ribs 392B converge on the second side 402.

The embodiments of a patellofemoral support advantageously overcome challenges of existing devices by providing a sleeve, buttress, and strap system arranged to cooperate with each other to apply forces and pressure in an effective, intuitive, and comfortable manner. A buttress and strap system may be configured to cooperate to apply forces to particular portions of a user's limb in a predetermined manner with optimal patella stabilization and/or immobilization and with greater ease of donning the device according to a user's dimensions. The embodiments of a patellofemoral support further allow for improved stabilization of a patellofemoral support and components thereof.

The invention claimed is:

1. A patellofemoral support, comprising: a sleeve defining at least two discrete regions having different elastic properties relative to one another, the sleeve having a knee area defining a knee center; a buttress connected to the sleeve and extending about the knee center of the sleeve corresponding to a patella of a user, the buttress having first and second branches extending along opposite sides of the knee center arranged along medial and lateral sides of a patella and proximally from a base located distally of the knee center, the base having an inner curvature corresponding to a general shape of a patella and arranged to abut a distal portion of the patella; a strap system including a helical strap and a circumferential strap, the helical strap is arranged to extend at an angle from a first side of one of a lateral or medial side of the sleeve and to pass over an anterior side of the sleeve to secure to a second side of a lateral or medial side opposite the first side in a distal direction, the circumferential strap extending between at least the first and second sides of the sleeve distally of the base of the buttress and the helical strap, and securing to at least one of the first and second sides without intersecting or overlapping the helical strap; wherein at least a portion of the strap system is arranged to extend over at least part of the first and second branches or base of the buttress and is arranged to exert forces upon the buttress from the first side of the sleeve to the second side of the sleeve generally between medial-to-lateral or lateral-to-medial directions; wherein a free end of the helical strap and a free end of the circumferential strap converge and are joined together by a strap tab, the strap tab carrying the free ends of the helical strap and the circumferential strap to removably connected attach to a plurality of locations within a tab landing area on the second side of the sleeve distal to the knee area, wherein the tab lan ding area has a larger shape than the strap tab: wherein the helical strap has an anchored end opposite to the free end, anchoring the helical strap to the first side of the one of the lateral or medial sides of the sleeve, the helical strap extending distally at a first location from the first side of the one of the lateral or medial side of the sleeve to the tab landing area at a second location on the second side of the sleeve, the circumferential strap extending from a third location on the first side of the one of the lateral or medial sides to the second location on the second side of the sleeve, the first location being proximal relative to the tab landing area and the third location.

2. The patellofemoral support of claim 1, further comprising a first stay panel extending along the first side, the first stay panel having greater rigidity than the sleeve.

3. The patellofemoral support of claim 2, further comprising a first strap interface connecting to the first stay panel, the first strap interface extending obliquely relative to the first stay panel, the helical strap extending from the first strap interface toward the second side.

4. The patellofemoral support of claim 3, wherein further comprising an extension interposed between the helical strap and the first strap interface, the extension having a different material property than the helical strap and the first strap interface.

5. The patellofemoral support of claim 4, wherein the extension is elastic.

6. The patellofemoral support of claim 5, wherein the helical strap is inelastic.

7. The patellofemoral support of claim 2, further comprising a second stay panel, the tab landing area defined by the second stay panel, and corresponding to a plurality of locations for attaching the strap tab to the second stay panel.

8. The patellofemoral support of claim 7, wherein the second stay panel includes an anti-attachment section arranged to prevent engagement with the strap tab and extends proximate to the tab landing area toward the anterior side of the sleeve.

9. The patellofemoral support of claim 2, further comprising a stay or a hinge at the first stay panel.

10. The patellofemoral support of claim 1, wherein the strap system is arranged to extend over the buttress asymmetrically.

11. The patellofemoral support of claim 10, wherein the helical strap is arranged to extend over a greater proportion of the first branch of the buttress relative to the second branch of the buttress.

12. The patellofemoral support of claim 1, wherein the knee area of the sleeve comprises a material having greater flexibility than an adjacent area to the knee area.

13. The patellofemoral support of claim 12, wherein the first and second branches and base extend around the knee area.

14. The patellofemoral support of claim 1, wherein the strap system only extends about the anterior side of the sleeve.

15. The patellofemoral support of claim 1, wherein the circumferential strap extends circumferentially about a distal circumference of the sleeve.

16. The patellofemoral support of claim 1, wherein the circumferential strap extends only between the first and second sides on the anterior side of a distal circumference of the sleeve.

* * * * *